United States Patent
Rose et al.

(10) Patent No.: US 11,301,993 B2
(45) Date of Patent: Apr. 12, 2022

(54) TREATMENT OF OCULAR DISORDERS USING A CONTENT GUIDE FOR VIEWING IMAGES

(71) Applicant: The Schepens Eye Research Institute, Inc., Boston, MA (US)

(72) Inventors: Dylan J. Rose, Medford, MA (US); Daniel R. Saunders, Boston, MA (US); Russell L. Woods, Boxborough, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 164 days.

(21) Appl. No.: 16/475,665

(22) PCT Filed: Feb. 17, 2018

(86) PCT No.: PCT/US2018/018564
§ 371 (c)(1),
(2) Date: Jul. 2, 2019

(87) PCT Pub. No.: WO2018/152454
PCT Pub. Date: Aug. 23, 2018

(65) Prior Publication Data
US 2020/0234432 A1      Jul. 23, 2020

Related U.S. Application Data

(60) Provisional application No. 62/460,156, filed on Feb. 17, 2017.

(51) Int. Cl.
*G06K 9/00*          (2006.01)
*A61B 3/14*          (2006.01)
(Continued)

(52) U.S. Cl.
CPC .............. *G06T 7/0012* (2013.01); *A61B 5/163* (2017.08); *A61B 5/4833* (2013.01); *A61B 5/742* (2013.01);
(Continued)

(58) Field of Classification Search
USPC ........ 382/100, 103, 106–107, 114, 117, 118, 382/128, 162, 172, 173, 181, 199, 209,
(Continued)

(56) References Cited

U.S. PATENT DOCUMENTS 8,851,678 B2 * 10/2014 Pelah ................... A61B 3/0041
                                                    351/224
2004/0105073 A1 * 6/2004 Maddalena ............ A61B 3/032
                                                    351/205
(Continued)

FOREIGN PATENT DOCUMENTS

WO         2015119630 A1     8/2015

OTHER PUBLICATIONS

Reducing Inattentional Blindness Using Subliminal Cueing in Visual Performance Tasks Deepti Pappusetty, Hari Kalva; Florida Atlantic University; Boca Raton, Florida/USA; 2016 Publication year 2016.*
International Search Report corresponding to International Patent Application No. PCT/US2018/018564, dated May 4, 2018, 14 pages.

*Primary Examiner* — Seyed H Azarian
(74) *Attorney, Agent, or Firm* — Mintz Levin Cohn Ferris Glovsky and Popeo, P.C.

(57) ABSTRACT

The current subject matter relates to rehabilitation using a content guide for viewing video, for example as a vision rehabilitation aid for individuals with hemianopia or as a rehabilitation aid for individuals with attention disorders. The current subject matter includes providing video in which a region of interest of the image is specified with a marker, referred to herein as a content guide. The content guide can include a circle surrounding the region of interest.

(Continued)

By providing video with a content guide to direct viewers to a region of interest in the video, information acquisition by the viewers is improved. Such an approach can aid individuals with vision deficits or attention disorders. The current subject matter can also be used as a therapy for spatial neglect. Related apparatus, systems, techniques and articles are also described.

23 Claims, 11 Drawing Sheets

(51) Int. Cl.
  *G06T 7/00* (2017.01)
  *A61B 5/16* (2006.01)
  *A61B 5/00* (2006.01)
(52) U.S. Cl.
  CPC ............... *G06T 2207/10016* (2013.01); *G06T 2207/10024* (2013.01); *G06T 2207/30041* (2013.01); *G06T 2207/30204* (2013.01)

(58) Field of Classification Search
  USPC ....... 382/214, 220, 224, 254, 276, 286–291, 382/305, 312; 600/303, 476; 351/224, 351/203, 205, 209; 514/617
  See application file for complete search history.

(56) References Cited

U.S. PATENT DOCUMENTS

| | | | |
|---|---|---|---|
| 2006/0164597 A1* | 7/2006 | Hayakawa | A61H 5/00 351/203 |
| 2009/0076156 A1* | 3/2009 | Husain | A61K 31/165 514/617 |
| 2010/0016730 A1* | 1/2010 | Tanaka | A61B 3/024 600/476 |
| 2015/0216414 A1* | 8/2015 | Wood | A61B 5/7475 600/303 |
| 2017/0360295 A1* | 12/2017 | Oz | G06K 9/3233 |

* cited by examiner

| (Survey questionnaire number), survey question | NV Mean (range)/proportion | Hemianopes Mean (range)/proportion | Statistical test of difference |
|---|---|---|---|
| (1) How many hours do you watch TV? | 2(0-5) | 2(0-6) | $p = 0.871$ |
| (3) Do you find it difficult when watching movies on the TV? | 24.2% 73/95 (yes/all) | 56.3% 49/87 | $\chi^2(4) = 23.64, p < 0.0001$ |
| (4) Do you use any special strategy? | 5.7% 3/53 | 30% 24/80 | $\chi^2(1) = 11.37, p = 0.001$ |
| (6) Do you ever watch TV, movies on a portable device? | 24.5% 40/163 | 30.6% 27/88 | $\chi^2(1) = 1.10, p = 0.294$ |
| (8) Do you have a computer at home? | 83.2% 109/131 | 91.3% 74/81 | $\chi^2(1) = 2.81, p = 0.093$ |
| (9) Do you ever watch DVDs on a computer? | 39.1% 45/115 | 53.3% 40/75 | $\chi^2(7) = 8.65, p = 0.278$ |
| (10) Do you ever watch videos on the internet? | 68.9% 80/116 | 62.6% 47/75 | $\chi^2(7) = 10.96, p = 0.140$ |
| (12) Do you find it difficult to see details when watching DVDs on a computer? | 11.6% 5/43 | 30.6% 19/62 | $\chi^2(4) = 8.85, p = 0.065$ |
| (13) Do you use assistive technology on your computer? | 2.2% 1/44 | 28.5% 18/63 | $\chi^2(4) = 12.56, p = 0.014$ |
| (15) How often do you go to the movie theater? | 81.2% 134/165 | 65.5% 57/87 | $\chi^2(6) = 14.61, p = 0.023$ |
| (16) Do you find it difficult to see details when watching movies at the theater? | 11.9% 11/92 | 44.5% 33/74 | $\chi^2(4) = 27.16, p < 0.0001$ |
| (18) How often do you take pictures? | 97.3% 73/75 | 67.5% 54/80 | $\chi^2(8) = 28.40, p < 0.0001$ |
| (22) Do you find it difficult to take a good picture? | 46.7% 35/75 | 51.4% 35/68 | $\chi^2(4) = 11.2, p = 0.024$ |

*FIG. 6*

TREATMENT OF OCULAR DISORDERS USING A CONTENT GUIDE FOR VIEWING IMAGES

RELATED APPLICATIONS

This application is a United States national stage application filed under 35 U.S.C. § 371, of International Patent Application No. PCT/US2018/018564, filed Feb. 17, 2018, which claims the benefit of and claims priority under 35 U.S.C. § 119(e) to U.S. Provisional Application 62/460,156 filed Feb. 17, 2017, and titled "Rehabilitation Aid and Treatment Using a Content Guide for Viewing Video", the entire content of each of which are hereby expressly incorporated by reference herein.

STATEMENT REGARDING FEDERALLY SPONSORED RESEARCH

This invention was made with government support under R01EY019100 awarded by the National Institute of Health and the National Eye Institute. The government has certain rights in the invention.

TECHNICAL FIELD

The subject matter described herein relates to methods of treatment for eye disorders.

BACKGROUND

Hemianopia, also known as hemianopsia, is a disorder in which there is a loss of vision in half the visual field of one or both eyes. The most common causes of this damage are stroke, brain tumor, and trauma. Hemianopia has a prevalence of ~0.8% in people over the age of 49 (Gilhotra J S, et al. *Journal of cerebral circulation* 2002; 33:2417-20). Between 8% (Gilhotra J S, et al. *Journal of cerebral circulation* 2002; 33:2417-20) and 26% stroke survivors have a visual field deficit, usually homonymous hemianopia.

In addition, there were about 5 million Americans with a permanent traumatic brain injury (TBI)-related disability in 2015 and about 6 million stroke survivors in 2010. Approximately 11,000 individuals are hospitalized in Veterans Health System facilities for acute stroke per year. About 33% of veterans with moderate to severe TBI have visual field loss. Up to 80,000 veterans are stroke survivors of which 30% to 50% have partial or complete homonymous hemianopia.

This vision impairment reduces the quality of life impacting activities of daily living, such as noticing other persons. Another activity that may be severely affected is watching video. Many people with hemianopia make horizontal scanning eye movements into their blind hemifield called compensatory eye movements. These can provide benefit to people with hemianopia during certain tasks. However, they may result in less time spent fixating highly-concentrated informative areas in video found with most commercial films and TV. This lowers information acquisition, which is the ability obtain and interpret the video content.

SUMMARY

The current subject matter relates to a method for reducing or treating one or more symptoms of hemianopia in a patient in need thereof. In aspects, the method comprises positioning the patient in front of a display, providing a video clip or an image on the display, marking (e.g., highlighting) a region of interest (e.g., region of interest) on the video clip or image with a content guide, and thereby reducing or treating one or more symptoms of hemianopia in the patient.

In embodiments, "treating" or "treatment" of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean inhibiting the progression of the condition, disorder or disease, slowing the progression of the condition, disorder or disease temporarily, although in some instances, it involves halting the progression of the condition, disorder or disease permanently.

As used herein, the terms "treat" and "prevent" are not intended to be absolute terms. In embodiments, treatment can refer to a 10%, 20%, 30%, 40%, 50%, 60%, 70%, 80%, 90%, or 100% reduction in the severity of an established disease, condition, or symptom of the disease or condition. In embodiments, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. In embodiments, references to decreasing, reducing, or inhibiting include a change of 10%, 20%, 30%, 40%, 50%, 60%, 70%, 80%, 90% or greater as compared to a control level and such terms can include but do not necessarily include complete elimination. In embodiments, the severity of disease is reduced by at least 10%, as compared, e.g., to the individual before treatment or to a control individual not undergoing treatment. In some aspects the severity of disease is reduced by at least 25%, 50%, 75%, 80%, or 90%, or in some cases, no longer detectable using standard diagnostic techniques.

"Patient" or "subject in need thereof" refers to a living member of the animal kingdom suffering from or who may suffer from the indicated disorder. In embodiments, the subject is a member of a species comprising individuals who may naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer.

In embodiments, the patient is positioned a defined distance, e.g., from about 10 cm to about 1000 in front of the display. The patient may be positioned about 10 cm, about 20 cm, about 30 cm, about 40 cm, about 50 cm, about 60 cm, about 70 cm, about 80 cm, about 90 cm, about 100 cm, about 200 cm, about 300 cm, about 400 cm, about 500 cm, about 600 cm, about 700 cm, about 800 cm, about 900 cm, about 1000 cm, about 2000 cm, about 3000 cm, about 4000 cm, or about 5000 cm in front of the display.

The video clip or image on the display may comprise a range of genres and types of depicted activities. Exemplary genres may include movies or videos of various durations or subjects, e.g., nature documentaries, cartoons, or dramas.

In an embodiment, the methods described herein further comprise calculating the Information Acquisition (IA) score of the patient comprising a hemianopia, and comparing the IA score of the patient comprising a hemianopia to a healthy patient. In an embodiment, the IA score of the patient comprising a hemianopia increases by about 0.5 shared (e.g., from the health patient), by about 1 shared word, by about 2 shared words, by about 3 shared words, by about 4 shared words, by about 5 shared words, by about 10 shared words, by about 20 shared words, by about 30 shared words, by about 40 shared words, by about 50 shared words, by about 100 shared words, by about 200 shared words, by about 300 shared words, by about 400 shared words, or by about 500 shared words.

In an embodiment, the IA score of the patient comprising a hemianopia increases by about 0.1 shared words to about 50 shared words. The IA score of the patient comprising a hemianopia increases by about 0.1 shared words to about 40 shared words, by about 0.1 shared words to about 30 shared words, by about shared 0.1 shared words to about 20 shared words, by about 0.1 shared words to about 10 shared words, by about 0.1 shared words to about 1 shared word, by about 0.1 shared words to about 0.5 shared words.

In an embodiment, the region of interest is determined by tracking the gaze (e.g., the eye movement) of a healthy patient. In an embodiment, the region of interest is determined by tracking the gaze (e.g., the eye movement) of a plurality of healthy patients.

In an embodiment, the video clip is about 30 seconds. In examples, the video clip is from about 5 seconds to about 180 seconds. In embodiments, the video clip is about 5 seconds, about 10 seconds, about 20 seconds, about 30 seconds, about 40 seconds, about 50 seconds, about 60 seconds, about 70 seconds, about 80 seconds, about 90 seconds, about 120 seconds, or about 180 seconds. The video can be of any length, for example, from shorter than 30 seconds to full-length feature movies or more. Viewing sessions can last from 10 seconds to 10 hours. In some embodiments, the viewing session is from about 5 minutes to an hour in duration. In some embodiments, the viewing session is about 5 minutes, about 10 minutes, about 20 minutes, about 30 minutes, about 40 minutes, about 50 minutes, about 60 minutes, about 70 minutes, about 80 minutes, about 90 minutes, about 120 minutes, or about 180 minutes. In some embodiments, two consecutive 30-minute clips can be used per treatment session. Multiple consecutive clips can improve patient engagement and compliance.

The content guide described herein may comprise a color. In embodiments, the color comprises yellow, red, black, white, cyan, or blue. In embodiments, the color includes a pop out or distinctive color. In embodiments, the content guide comprises multiple colors. The content guide described herein may comprise a shape. In embodiments, the shape is a circle, rectangle, outline, polygon, two hemicircles, and the like. The content guide described herein may vary with content. For example, as the region of interest becomes larger, the content guide can become larger. As another example, as the region of interest becomes smaller, the content guide can become smaller. In embodiments, the content guide comprises an enhanced contrast or other image enhancement. In embodiments, the content guide includes characteristics to catch the attention of the viewer and can be readily visible and easy to follow.

In embodiments, the region of interest is updated about every 0.017 to 5 seconds. In examples, the region of interest is updated about every 0.033, 0.066, 0.0099, 0.0132, 0.0165, 0.0198, 0.0231, 0.0264, 0.0297, 0.033, 0.0363, 0.0396, 0.0429, 0.0462, 0.0495, 0.0528, 0.0561, 0.0594, 0.0627, 0.066, 0.0693, 0.0726, 0.0759, 0.0792, 0.0825, 0.0858, 0.0891, 1, 2, 3, 4, 5, 6, 8, 10 seconds, about every 20 seconds, about every 30 seconds, about every 60 seconds, about every 90 seconds, or about every 120 seconds or more. In embodiments, the region of interested is updated about every frame. For example, the region of interest is updated at the standard video frame rate of about 30 Hz (e.g., every 0.033 seconds). There is video content (e.g. progressive scan) at faster rates (e.g. 60 Hz, so 0.017 second updating) and there is slower video content (used sometimes to reduce bandwidth transmission problems and sometimes because the original material was recorded at a slower rate (some older or non-"standard")).

In some embodiments, the display comprises a portable device (e.g., an iPhone, an iPad, an iPod, or a personal DVD player), a computer, a cinema screen, a photograph, or a television. In some example, the mobile device is a portable computing device, e.g., a computing device that is small enough to hold and operate in the hand, such as a device that is smaller than 20 inches by 15 inches by 4 inches and weighs less than 10 pounds. Some non-limiting examples of computing devices are a mobile phone, a tablet computer, or a laptop computer.

The methods for reducing or treating one or more symptoms of hemianopia described herein are the result of a traumatic brain injury (TBI), a stroke (e.g., ischemic stroke or hemorrhagic stroke), and a stroke during surgery, or a brain tumor. Other causes of hemianopia include neurosurgery, papilledema, transient ischemic attacks, multiple sclerosis, infections (encephalitis, abscess), degenerative dementia (posterior cortical atrophy), Creutzfeldt Jakob disease, adrenoleukodystrophy, seizures, and severe hyperglycemia.

In aspects, provided herein are methods for reducing or treating one or more symptoms of a cognitive disorder in a patient in need thereof. The method comprises positioning the patient in front of a display, providing a video clip or an image on the display, marking (e.g., highlighting) a region of interest on the video clip or image with a content guide, and thereby reducing or treating one or more symptoms of the cognitive disorder in the patient.

In embodiments, the patient is positioned from about 10 cm to about 1000 in front of the display. The patient may be positioned about 10 cm, about 20 cm, about 30 cm, about 40 cm, about 50 cm, about 60 cm, about 70 cm, about 80 cm, about 90 cm, about 100 cm, about 200 cm, about 300 cm, about 400 cm, about 500 cm, about 600 cm, about 700 cm, about 800 cm, about 900 cm or about 1000 cm in front of the display. In some examples, the subject is about 100 cm in front of a display. Such devices/configurations are useful to present a video. Most people sit further than 1 m from their TV, the most common being 3 to 4 m. Portable devices (e.g. tablets, laptops, phones) are viewed at closer distances such as 30 to 60 cm, e.g, 30-50 cm. Cinema screens are viewed from considerably longer viewing distances, probably from a few metres to 40 m (depends on cinema size). Thus, the subject can be 10 cm to 50 meters from the video or moving picture display. In other embodiments, even static images can be enhanced for a hemianopic viewer with a content guide.

In embodiments, the cognitive disorder comprises hemispatial neglect, spatial neglect, Attention Deficit Hyperactivity Disorder (ADHD), Attention Deficit Disorder (ADD), Alzheimer's disease, or dementia.

In aspects, provided herein are methods for reducing or treating one or more symptoms of spatial neglect in a patient in need thereof. In embodiments, the method comprises positioning the patient in front of the display, providing a stimulus on the display, moving the stimulus within the display, and instructing the patient to follow the stimulus on the display, and thereby reducing or treating one or more symptoms of spatial neglect in the patient.

In embodiments, stimulus may be moved in a horizontal motion, a vertical motion, or a circular motion. In embodiments, the moving stimulus may be referred to as a dynamic cue.

In embodiments, the stimulus comprises a visual prompt, e.g. dots or sets of dots or a prompt of any geometric shape, e.g., a square, rectangle, triangle or other shape.

In embodiments, the method is continued for about 5 minutes to about 180 minutes. In embodiments, the method is continued for about 10 minutes to about 180 minutes, for about 20 minutes to about 180 minutes, for about 30 minutes to about 180 minutes, for about 40 minutes to about 180 minutes, for about 50 minutes to about 180 minutes, for about 60 minutes to about 180 minutes, for about 90 minutes to about 180 minutes, or for about 120 minutes to about 180 minutes.

The method may be continued for about 10 minutes, for about 20 minutes, for about 30 minutes, for about 40 minutes, for about 50 minutes, for about 60 minutes, for about 90 minutes, or for about 120 minutes or more.

In embodiments, the method may be continued to the patient 1, 2, 3, 4, 5, 6, 7, 8, 9, 10, 11, 12, 13, 14, 15, 16, 17, 18, 19, 20 or more times, or any range derivable therein, and they may be continued every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein.

In embodiments, the method may be continued once daily, twice daily, three times daily, four times daily, five times daily, or six times daily (or any range derivable therein) and/or as needed to the patient. The method may be continued every 24 hours, every 48 hours, or every 96 hours.

In embodiments, the method is continued on a regime of every four days, every week, every 10 days, every 14 days, every month, every 2 months, every 3 months, or every 4 months.

In embodiments, the spatial neglect is associated with hemianopia. In embodiments, the spatial neglect is not associated with hemianopia.

The current subject matter relates to rehabilitation using a content guide for viewing video, for example as a vision rehabilitation aid for individuals with hemianopia or as a rehabilitation aid for individuals with attention disorders or as a treatment for spatial neglect. The current subject matter includes providing video where a region of interest within the image is specified with a marker, referred to herein as a content guide. The content guide can be represented by a circle or other marker surrounding the region of interest. An area of the content guide can varying in shape and location between video frames. By providing video with such a content guide, information acquisition by viewers is improved. Such an approach can aid individuals with vision deficits or attention disorders. The current subject matter can also be used as a therapy for spatial neglect.

In some examples, the methods, devices or systems are used as a rehabilitation aid, e.g., for subjects with hemianopia. For example, the clinical condition of hemianopia remains substantially unaltered (e.g., the subject's field of vision does not increase/improve); however, the methods provide a significant benefit to the subject by improving their ability to cope with their condition, i.e., their ability to avoid bumping into objects, improving their ability to navigate in their homes or other surroundings or environments, their ability to enjoy and absorb information from their surroundings, entertainment sources, or educational sources (e.g., videos). As a result, quality of life of such individuals is improved. As a rehabilitation aide, the subjects watch the videos containing the content guide or dynamic cue at will, i.e., the schedule or duration of viewing is as little or as often as the subject chooses. For example, the subject may choose to spend several hours watching movies containing the content guide or dynamic cue. The methods, devices, and systems lead to a reduction in the disability of daily living. Used as a rehabilitation aide, a subject experiences an improvement in immediate symptoms while watching the video or movie picture display, e.g., thereby increasing comprehension and/or enjoyment.

The methods, devices, or systems are also used for therapy and lead to improvement in a clinical condition, e.g., spatial neglect. Spatial neglect is a common syndrome following stroke, most frequently of the right side of the brain. Such patients fail to be aware of objects or people to their left. For example, when searching through a visual scene, patients with left neglect tend to look at elements on the right only. Spatial neglect involves the inability to report, respond, or orient to stimuli, generally in the contralesional space. Neglect is primarily a disorder of attention whereby patients fail to orientate, to report or to respond to stimuli located on the contralesional side. Methods of diagnosing and evaluating this condition are known in the art, e.g., Li et al., Pract Neurol. 2015 October; 15(5): 333-339. The methods and systems described herein are useful to treat this condition, thereby leading to clinical recovery as well as a reduction in the level of disability associated with daily living. A therapy protocol or plan can take place in a clinical setting such as a clinic or hospital or can take place at home, e.g, with a prescription or directive to watch a video clip or series of video clips for a prescribed period of time. The videos range in duration. Exemplary clinical protocols may involve watching daily, every other day, or multiple times a day (e.g., 2, 2, 4, 5 times) a video of a prescribed duration, e.g., 5 min., 0.5 hr, 1 hr per day. For example, the subject/patient is prescribed to undergo 1 hour of training (video watching) per day, e.g, one 1 hour segment/video clip or multiple shorter clips, e.g., two 30 minute clips, e.g., several 15 minute clips. The nature of the subject matter and duration of clips may vary depending on the age, cognitive capability, education, and/or interest of the subject. In some examples, multiple clips lead to improved engagement and therefore better patient compliance. Used as a therapy, the subject experiences a carry-over effect, e.g., after training, the patient experiences an improvement in the clinical condition from which the subject suffers (e.g., spatial neglect). For example, dynamic cue training actually changes perception on the patient's "bad"/neglected side. Such improved perception is evaluated, e.g., using standard tests for neglect such as performance in tasks such as walking and/or reading.

In some aspects, the current subject matter, which can include technology that finds and creates the region of interest in a video, can be used to create a therapy for spatial neglect and other vision impairments. By following the region of interest while watching the video induces a patient with spatial neglect to look into the neglected side that they would not otherwise view. Existing therapies for these conditions involve watching moving lights and lack the interested provided by more entertaining media. Videos marked with regions of interest can provide a more engaging form of therapy.

In some aspects, the current subject matter includes emphasizing or indicating a region dynamically in a video and using it for clinical purposes.

In an aspect, a method includes receiving data characterizing a video, determining a region of interest of the video, and providing the video and region of interest as an aid for improving viewer information acquisition.

One or more of the following features can be included in any feasible combination. The region of interest can be a stimulus highlighting content of interest in the video. The region of interest can be a marker that is displayed or superimposed on top of the video. The marker can include a circle, hemi-circle(s), a rectangle, an illusory rectangle (e.g., Kanizwa figure that shows only the "corners" of a rectangle), a polygon that can vary in shape with variations in the characteristics of the region of interest, image enhancements (such as increased local contrast or edge enhancement), and the like. The marker can vary in size with variations in the region of interest. Providing the video and region of interest can include displaying the video and region of interest as a content guide to viewers with hemianopia. Providing the video and region of interest includes displaying the video and region of interest as a content guide to viewers with other attention deficits unrelated to hemianopia. The region of interest is provided as an attention-disorder or vision-deficient rehabilitation aid. Providing the video and region of interest includes displaying the video and region of interest as a dynamic cue to viewers with spatial neglect that may be associated with hemianopia or found without hemianopia. The region of interest is provided as a spatial neglect treatment. Determining the region of interest can include measuring gaze patterns of normal individuals, determining the region of interesting using an image processing algorithm, and the like. The video can be displayed on a television, computer or other electronic device screen.

In another aspect, a system for improving video viewer information acquisition includes memory storing data characterizing a video and a region of interest, at least one data processor coupled to the memory and configured to combine the region of interest and the video, and a display providing the video and region of interest as an aid for improving viewer information acquisition.

In an aspect, a system is provided for reducing or treating one or more symptoms of hemianopia or spatial neglect in a patient in need thereof, the system comprising: a display configured to provide a video clip or an image and to mark a region of interest on the video clip or image with a dynamic cue or content guide thereby reducing or treating one or more symptoms of hemianopia or spatial neglect in the patient.

In embodiments, the system further includes a camera configured to acquire an image of the patient when the patient is positioned in front of the display. In embodiments, the system further includes facial recognition circuitry configured to identify, using the acquired image, an identity of the patient to assess compliance with a spatial neglect or hemianopia treatment protocol.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 6 illustrates a summary of video viewing habits compared between the hemianopia group (N=93) and normally-sighted (NV) group (N=193) for a particular study.

Like reference symbols in the various drawings indicate like elements.

DETAILED DESCRIPTION

Figure 1:
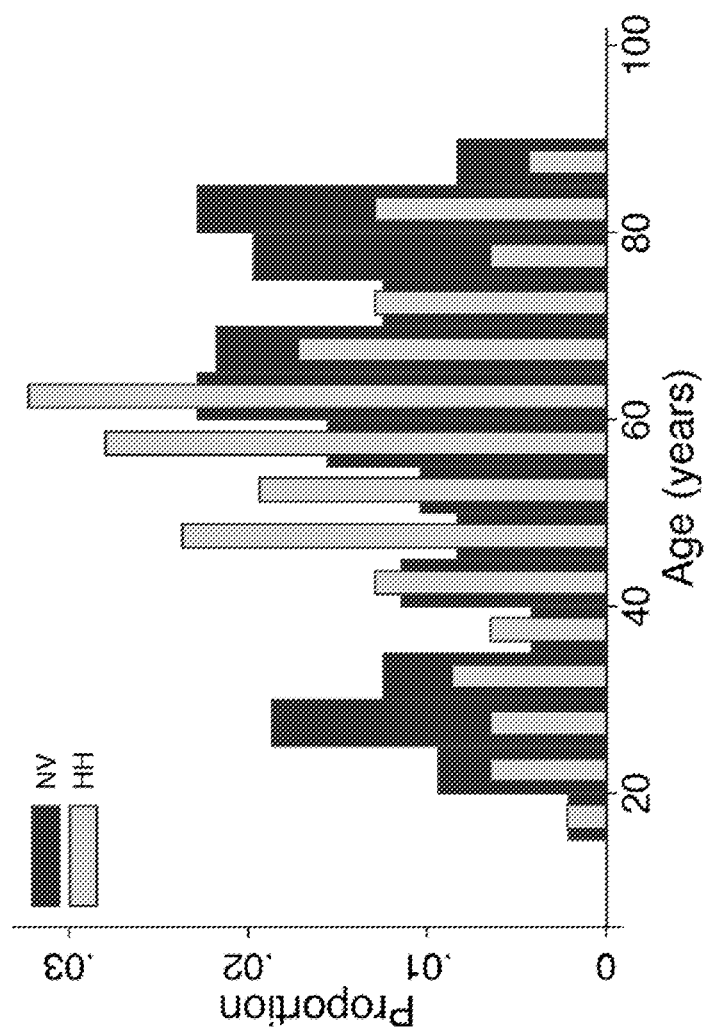
FIG. 1 illustrates age distribution of participants in a survey (Study 1).

The current subject matter relates to rehabilitation using a content guide for viewing video, for example as a vision rehabilitation aid for individuals with hemianopia or as a rehabilitation aid for individuals with attention disorders. The current subject matter includes providing video in which a region of interest of the image is specified with a marker or otherwise manipulated digitally, referred to herein as a content guide. By providing video with a content guide to direct viewers to a region of interest in the video, information acquisition by the viewers is improved. Such an approach can aid individuals with vision deficits or attention disorders.

It has been demonstrated that Hemianopia patients acquire more information from watching video with a content guide than from watching video without a content guide. The content guide can improve Hemianopia patients' enjoyment of video. In addition, the content guide can be a useful educational tool for individuals suffering from Attention Deficit Hyperactivity Disorder and other attention disorders.

In order to implement the content guide, the region of interest of an image can be determined. The region of interest can be determined by measuring the gaze patterns of normal individuals. The region of interest can be determined using other approaches, such as using image processing software.

Hemianopia is a common outcome of stroke and other brain injuries. People with hemianopia report difficulty watching TV. Three related studies are discussed. (1) A survey about watching TV and movies showed that people with hemianopia were more likely to report difficulty watching video on TV, a computer or in a theater, and were less likely to watch video on a computer, attend the theater or take photographs than people with full sight. (2) The ability to follow the story in video clips was measured, by automatically scoring their descriptions of the clips using a wisdom-of-the-crowd approach. Participants with hemianopia had more difficulty following the story than the participants with full sight. (3) A vision rehabilitation aid was deployed for people with hemianopia (the content guide). Their ability to follow the story was improved by the content guide. Combined, these results show that patients with hemianopia not only report difficulty viewing video, but that deficit can be measured, and interventions like the content guide may help them follow the story and thus improve their enjoyment.

Example 1

Information acquisition is the gathering and interpretation of sensory information. An exemplary method for measuring this ability in humans uses free-recall responses to sensory stimuli which are scored objectively. (Saunders et al. PLoS One. 2014 Apr. 2; 9(4):e93251. doi: 10.1371/journal.pone.0093251. eCollection 2014). This metric can be evaluated using perception of video stimuli. For example, immediately after viewing a video clip, subjects are asked to respond to a prompt to give a short description of the clip in natural language. These responses are scored automatically by comparison to a dataset of responses to the same clip by normally-sighted viewers (control or standard). A simple count of the words in common is used to determine performance of the test subject. This approach, of scoring open-ended immediate free recall of the stimulus, is applicable not only to video, but also to other situations where a measure of the information that is successfully acquired is desirable. Information acquired is affected by stimulus quality, sensory ability, and cognitive processes, so the metric can be used to assess each of these components when the others are controlled.

People with homonymous hemianopia report difficulty watching TV, but this difficulty has not been systematically investigated. Their reported difficulty is characterized, objectively measured, and an evaluation of the content guide, novel rehabilitation aid, is described. A survey was conducted about watching TV and movies with subjects with normal vision (N=193) or hemianopia (N=93). The ability to follow the story in video clips in a subset was measured from both groups (N=60, 20, respectively), using an information acquisition measure that takes a natural-language-processing approach to objectively scoring the subject's descriptions of the clips. The information acquisition of subjects with hemianopia (N=17) was compared when viewing the videos with or without a superimposed dynamic cue (the content guide).

Subjects with hemianopia were more likely to report difficulty watching TV, movies on a computer, and movies at the theater, and were less likely to take photographs, because of vision difficulties. The hemianopia group had a significantly lower information acquisition score (shared word score), average 3.0, compared to 4.3 of the normal-vision group (mixed-effects regression, $z=4.52$, $p<0.001$). Presence of the content guide significantly increased the IA score by 0.54 shared words ($z=4.67$, $p<0.001$) and was higher in most (14/17) of the subjects with hemianopia.

Patients with hemianopia reported more difficulty with viewing video, that can be objectively demonstrated (reduced information acquisition score), and interventions like the content guide may provide benefit.

Homonymous hemianopia is a cortical blindness, most commonly from stroke, that eliminates all vision on one side in both eyes, thus reducing visuo-spatial perception. This vision impairment reduces the quality of life impacting activities of daily living, such as noticing other persons (Meienberg O, et al. (1981) *Ann Neurol* 9:537-544), walking (Gall C, et al. (2009) *Invest Ophthalmol Vis Sci* 50:2765-2776; Yates J S, et al. (2002) *J Rehabil Res Dev* 39:385-394), and driving (Papageorgiou E, et al. (2007) *Graefes Arch Clin Exp Ophthalmol* 245:1749-1758; Bowers A R, et al. (2009) *Invest Ophthalmol Vis Sci* 50:5137-5147; Chen C S, et al. (2009) *Top Stroke Rehabil* 16:445-453; Gall C, et al. (2009) *Invest Ophthalmol Vis Sci* 50:2765-2776; Wood J M, et al. (2009) *Invest Ophthalmol Vis Sci* 50:577-585; Gall C, et al. (2009) *Invest Ophthalmol Vis Sci* 50:2765-2776). Another activity that can be severely affected is watching TV and other forms of video. A survey of 46 people with hemianopia and quadranopia, that included one question about television, found that 30 percent reported some difficulty with watching television (Warren M (2009) *Am J Occup Ther*

63:626-633). Older adults are most at risk of stroke, and also spend the most time watching TV in the U.S.A; over 49 hours a week on average for people 65 years and older. Therefore, it is important to understand the scale of this problem, to investigate its causes, and to develop treatments or aids. Many rehabilitation strategies have been adopted for people with hemianopia, including vision restitution, compensation (e.g. scanning training) and substitution (e.g. prisms) (Nelles G, et al. (2001) *Neurosci Lett* 306:189-192; P Pambakian A, et al. (2005) *J Neuroophthalmol* 25:136-142; Jobke S, et al. (2009) *Neurorehabil Neural Repair* 23:246-255; Roth T, et al. (2009) *Neurology*. 72:324-331; Pollock A, et al. (2011) Cochrane Database Syst Rev CD008388; Hayes A, et al. (2012) *NeuroRehabilitation* 31:19-30; Bowers A R, et al. (2014) *JAMA Ophthalmol*.132: 214-222; de Haan G A, et al. (2015) *PLoS One* 10:e0134459.; Matteo B M et al. (2016) *J Vision*. 16:11) with evidence of benefit from some (Jobke S, et al. (2009) *Neurorehabil Neural Repair* 23:246-255; de Haan G A, et al. (2015) *PLoS One* 10:e0134459; Bowers A R, et al. (2014) *JAMA Ophthalmol*.132:214-222) but not all (Reinhard J, et al. (2005) *Br J Ophthalmol*. 89:30-35; Roth T, et al. (2009) *Neurology*. 72:324-331) recent randomized trials.

Described here is the first systematic survey of people with hemianopia (HH; N=93) that is focused on watching video, including their consumption of various forms of video and the degrees of difficulty they experience. This survey also includes questions related to their habits taking photographs and going to the theater to watch movies. 193 people with normal vision (NV) were included as a control group.

In addition to subjective reports of difficulty watching TV, in the second part of this study objective deficits in the ability of a subset of the hemianopia group (N=20) to derive information from segments of movies and TV programs, relative to viewers without hemianopia (N=61) were measured. A technique that involves eliciting open-response, natural-language descriptions of short video clips, which are then automatically scored relative to a database of responses by normally-sighted individuals was used (Saunders D R, et al. (2013) *J Med Internet Res* 15:e100, Saunders D R, et al. (2014a) *PLoS One* 9:e93251). The metric that is produced, the information acquisition score, has been shown to be sensitive to degradation of the video due to optical or video-processing blurring (Saunders D R, et al. (2014a) *PLoS One* 9:e93251) and to central vision impairment (Saunders D R, et al. (2014b) 11*th International Conference on Low Vision* 2014; Melbourne, Australia), and therefore was suitable for detecting differences in information acquisition resulting from hemianopia, an impairment of peripheral vision.

Once the reduced ability to obtain information from video is established for people with hemianopia, the question remains of the immediate causes of this problem. One possibility is due to their eye movement (or gaze) patterns. Commonly, people with hemianopia make horizontal scanning eye movements into their blind hemifield, which have been called compensatory eye movements. These gazes into the blind side can provide benefit to people with hemianopia during certain tasks (Nelles G, et al. (2001) *Neurosci Lett* 306:189-192 Iorizzo D B, et al. (2011) *Vision Res* 51:1173-1184). However, these scans may result in less time fixating the highly-concentrated informative areas in video found with most commercial films and TV (Goldstein R B, et al. (2007) *Comput Biol Med* 37:957-964, Dorr M, et al. (2010) *J Vis* 10:28), which could lower information acquisition. Therefore, a way to help people with hemianopia to watch TV may be to guide their eye movements to remain in these highly informative regions, and to discourage compensatory scanning away from the region of interest. In the third study, a new method is described, using a dynamic cue based on the region of interest that was derived from the eye movements (gaze pattern) of normally-sighted viewers viewing that video, to create a cue that is overlaid on the video, which is called a "content guide." It can guide the gaze of a person with hemianopia to these "crowd-sourced" locations of significant interest over the course of the video, so that objects of interest are not lost in the scotoma (blind side) and indicating that the gaze need not be to the blind side (so compensatory eye movements are not required). With the content guide present, there can be an increase in the amount of information that was acquired, as measured by the information acquisition score.

Study 1: Survey

The survey was based on investigating the viewing habits of people with impaired central vision. It was administered either in person or as a telephone interview. Verbal consent from each participant was obtained for the telephone-administered survey after the study was explained and the consent form was read out. Written consent was obtained from participants who took the survey in person. The questions were verbally asked and all the choices were read out before the participant could choose an answer. In addition to demographic and clinical questions, there were total of 23 questions related to viewing habits and the survey took about 10 to 15 minutes to complete. Data collection was administered by an examiner using a custom FileMaker Pro5.5 (FileMaker Inc., Santa Clara, Calif., USA) interface with a layout like a paper-based form. The verbal responses were recorded in the electronic file by the examiner.

Of the 286 participants, 193 were normally-sighted and 93 had some type of hemianopia (see Table 1), 205 were administered the survey by telephone call and 81 in person. As shown in FIG. 1, there were younger (20 to 35 years) and older (75 to 85 years) participants in the normal-vision sample (Kolmogorov-Smirnov two-sample, p=0.02). Age was included as a covariate in analyses. There was no difference in education (p=0.21) or gender (p=0.11) between the two groups. See Table 1 with descriptive demographic and clinical information of all the participants.

TABLE

Self-reported demographic, clinical, and visual characteristics of participants (N = 286). TBI = traumatic brain injury.

|  |  | NV | HH |
|---|---|---|---|
| N |  | 193 | 93 |
| Gender | Male | 83 | 53 |
|  | Female | 87 | 39 |
|  | Not recorded | 23 | 1 |
| Race | Asian | 11 | 1 |
|  | African American | 19 | 1 |
|  | White | 128 | 65 |
|  | American Indian | 2 | 0 |
|  | Not recorded | 32 | 24 |
| Age | | 57.04 y | 56.33 y |
| (mean, min-max) | | (19-87 y) | (19-86 y) |
| Education level | <high school | 1 | 2 |
|  | High school | 12 | 11 |
|  | Some college | 11 | 16 |
|  | Technical | 1 | 4 |
|  | Associate | 2 | 5 |
|  | Bachelor's | 31 | 20 |
|  | Master's | 29 | 19 |
|  | Professional | 5 | 7 |

TABLE-continued

Self-reported demographic, clinical, and visual characteristics of participants (N = 286). TBI = traumatic brain injury.

|  |  | NV | HH |
|---|---|---|---|
|  | Doctoral | 8 | 5 |
|  | Not recorded | 90 | 4 |
| Visual Acuity Right Eye |  | 22(9) | 25(12) |
| Left Eye |  | 22(8) | 26(12) |
| Both Eyes |  | 19(5) | 23(16) |
| Vision Loss | Central | N/A | 2 |
|  | Right hemi |  | 31 |
|  | Left hemi |  | 55 |
|  | Bitemporal |  | 2 |
|  | Not recorded |  | 5 |
| Cause | Stroke |  | 57 |
|  | Ischemic |  | 17 |
|  | Hemorrhagic |  | 6 |
|  | Unknown |  | 33 |
|  | TBI |  | 10 |
|  | Tumor |  | 12 |
|  | Surgery |  | 10 |
|  | Congenital |  | 2 |
|  | N/A |  | 4 |

Study 2: Information Acquisition Method

The method for determining information acquisition included methods described in U.S. application Ser. No. 14/426,314, the entire contents of which is hereby expressly incorporated by reference herein.

Participants viewed twenty 30-second video clips (described below) on a 27-inch display (aspect ratio 16:9) from 100 cm, so the videos were 33° of visual angle wide. The clips were displayed by a MATLAB program using the Psychophysics Toolbox (Brainard D H (1997) *The Psychophysics Toolbox. Spat Vis* 10:433-436) and Video Toolbox (Pelli D G. *Spatial Vision* 1997; 10(4):437-42). An experimenter gave the instructions and was in the room during data collection, but the MATLAB program automatically displayed the prompts after viewing each clip, asking the participant to provide verbal response to the open-ended queries "Describe this movie clip in a few sentences, as if to someone who has not seen it" and then, "List several additional visual details that you might not mention in describing the clip to someone who has not seen it.". Participants were instructed to report on the visual aspects of the clip. The spoken responses to each prompt were recorded using a headset microphone and later transcribed using MacSpeech Pro to produce an initial (automated) transcript. A group of Mechanical Turk workers then verified and corrected the automated transcript (Marge et al., 2010).

These natural-language responses were transcribed and automatically scored for their relevant content using a "wisdom of crowds" approach described previously (Saunders D R, et al. (2013) *J Med Internet Res* 15:e100; Saunders D R, et al. (2014a) *PLoS One* 9:e93251) to determine the information acquisition (IA) score. The text of responses were processed with the Text to Matrix Generator toolbox for MATLAB (see descriptions in Saunders D R, et al. (2014a) *PLoS One* 9:e93251 and Saunders D R, et al. (2013) *J Med Internet Res* 15:e100). Each response was compared to all the responses to the same video clip in a database of responses from 159 subjects that contained as least 32 responses per video clip (Saunders, et al. 2013). It was reasoned that if a response contained accurate content about the clip, then on average it should be similar to other responses to the same video clip.

The number of words that two responses shared (after removing stopwords), disregarding repeated instances of the word in either response, produced a shared-word count for each pair. The IA score for each subject was the average of the shared-word counts from the paired comparison with each of the responses from the database for the same clip and then averaged over all of the video clips seen by the participant (typically, 640 comparisons=32×20).

Study 2 participants were recruited from the community in and near Boston, Mass., using a contact list or by being referred by physicians or by participants in this and other studies. All had participated in the survey. There were 20 participants with hemianopia. For 12 of the subjects, the blind hemifield was the left side, while for 8 the blind hemifield was the right side. Five participants with hemianopia were female, and the median age was 62 years (range 19-81 years). They were recruited from local clinics or had participated in other studies at the Schepens Eye Research Institute. All had homonymous hemianopia, with the criteria that none had a projection of sight of more than 10 degrees into the blind hemifield within the central 30 degrees of vision. Six subjects showed evidence of hemispatial neglect and a further two had a previous history of neglect. The cause of the hemianopia was a stroke not during surgery for twelve participants (five ischemic, two hemorrhagic, and five unknown), a stroke during surgery for two participants, traumatic brain injury (TBI) for four participants, and a brain tumor for two participants. One of the participants with hemianopia also had glaucoma but without an absolute scotoma associated with it (also participated in Study 3). This sample was not different from the rest of the subjects with hemianopia who participated in Study 1 (p≥0.18), though there was a tendency for there to be a larger proportion of males in study 1 ($\chi2(1)$=3.17, p=0.075). None of these 20 participants with hemianopia had expressive aphasia, being able to hold a conversation and name objects.

Sixty people with no ocular conditions in self-reported ophthalmic history, no visual field defects, normal appearance of retina, and binocular visual acuity better than 20/32 constituted a control group. The median age of this group was 57 (range 19-87) years and 38 were male. This sample was not different from the rest of the subjects with normal sight who participated in Study 1 (p=0.005) and its age distribution did not differ significantly from the people with hemianopia group.

All participants, normal-vision and hemianopia, had Montreal Cognitive Assessment (MoCA) (Nasreddine Z S, et al. (2005) *J Am Geriatr Soc* 53:695-699) score above 20, indicating no evidence of significant cognitive deficits that could interfere with information processing or language production. MOCA score was included as a covariate in analyses and was not significant. The hemianopia group had a higher proportion of males ($\chi2(1)$=3.81, p=0.05) and a lower maximum education (Mann-Whitney, z=3.2, p=0.001) compared to the normal-vision group, but there were no differences in age (Kolmogorov-Smirnov, p=0.69), MoCA scores (Mann-Whitney, z=1.34, p=0.18) or visual acuity scores (Mann-Whitney, z=0.52, p=0.60). Informed consent was obtained from each participant prior to data collection. Participants were shown the video clips wearing habitual, not necessarily optimal, optical correction.

Figure 8:
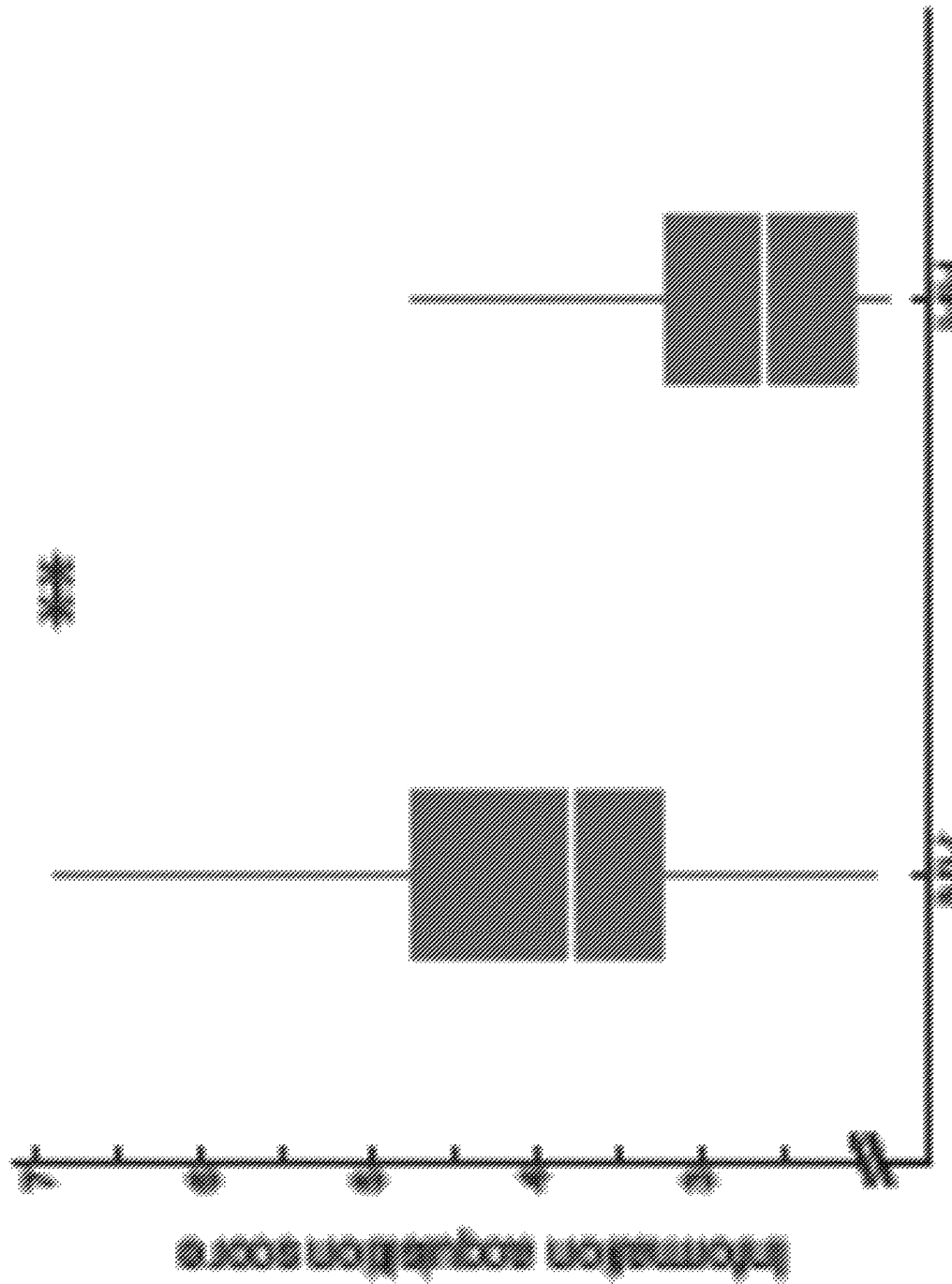
FIG. 8 illustrates the information acquisition (IA) score difference between normal vision and homonymous hemianopia.

In a similar study, participants with HH, on average, had an IA score that was 1.59 shared words lower than the normal-vision participants (mixed-effect regression, z=5.79, p<0.001), when corrected for age (2.74 shared words vs. 4.33 shared words). FIG. 8 illustrates the IA score difference between NV and HH.

Study 3: Content Guide

To follow up on the observations that some of the problems reported by (Study 1) and measured in (Study 2) people with hemianopia could be ameliorated by providing guidance on the locations in which important information could be found, studies of the content guide method were conducted. The content guide showed the objects of interest as determined from the gaze patterns of normally-sighted viewers. The content guide removes the need to make compensatory scanning eye movements into the blind side (made to check whether there are objects of interest that were otherwise not visible).

To determine objects of interest in each video clip, the region of interest (also referred to as a center of interest (COI)) was found by tracking the gaze of viewers with normal vision using an EyeLink 1000 system (SR Research Ltd., Mississauga, Ontario, Canada). At least 15 of the 61 subjects with normal vision watched each video clip. Saccades and blinks were removed from the data and computed the smoothed median gaze location for each video frame. A kernel density estimate of the fixation points for a specific frame is shown in FIG. 2A.

For this pilot study, a thin yellow ring centered over the COI was presented as the content guide (FIG. 2B) in the first or second of two blocks (20 clips per block, with clips and blocks randomly and evenly distributed). The IA scores were compared between these two viewing conditions (presence or absence of the content guide). Additionally tested were whether the order in which the content guide was presented (first or second block) played an effect in the IA scores (e.g. fatigue effect).

Seventeen of the participants with hemianopia from Study 2 also participated in Study 3. For nine of the subjects, the blind hemifield was the left side, 5 were female, and the median age was 62 years (range 20 to 81) years. Only one showed evidence of hemispatial neglect. The cause of the hemianopia was TBI for 2 participants, a stroke during surgery for 2 participants, a stroke not during surgery for 11 participants (five ischemic, two hemorrhagic, and four unknown), and a brain tumor for 1 participant.

There were 40 video clips, chosen to represent a range of genres and types of depicted activities. The genres included nature documentaries (e.g., BBC's Deep Blue, The March of the Penguins), cartoons (e.g., Shrek, Mulan), and dramas (e.g., Shakespeare in Love, Pay it Forward). The clips were 30 seconds long and were selected from parts of the films that had relatively few scene cuts, which was reflected in the average number of cuts per minute in our clips being 9, as compared to approximately 12 per minute in contemporary films (Cutting J E, et al. (2010) *Psychol Sci* 21:432-439). The clips included conversations, indoor and outdoor scenes, action sequences, and wordless scenes where the relevant content was primarily the facial expressions and body language of one or more actors.

Comparisons between the hemianopia and control groups for the survey questions (Study 1) used logistic regression (LR) and ordered logistic regression (OLR) as these allowed inclusion of covariates age, education level and gender. To compare IA scores between groups (with and without hemianopia; Study 2) and the effect of the content guide (Study 3), mixed-model regression analyses (Janssen D P (2012) *Behav Res Methods* 44:232-247) was used with "participant" and "video clip" as random factors, and demographic information (e.g. gender, age), MOCA score and visual acuity as covariates. Block order was a fixed factor in the analysis of the content guide. To compare the IA scores to the survey responses mixed-model regression analyses were used, with demographic information, MOCA score and visual acuity as covariates.

Hemianopis TV Survey Results

Figure 3:
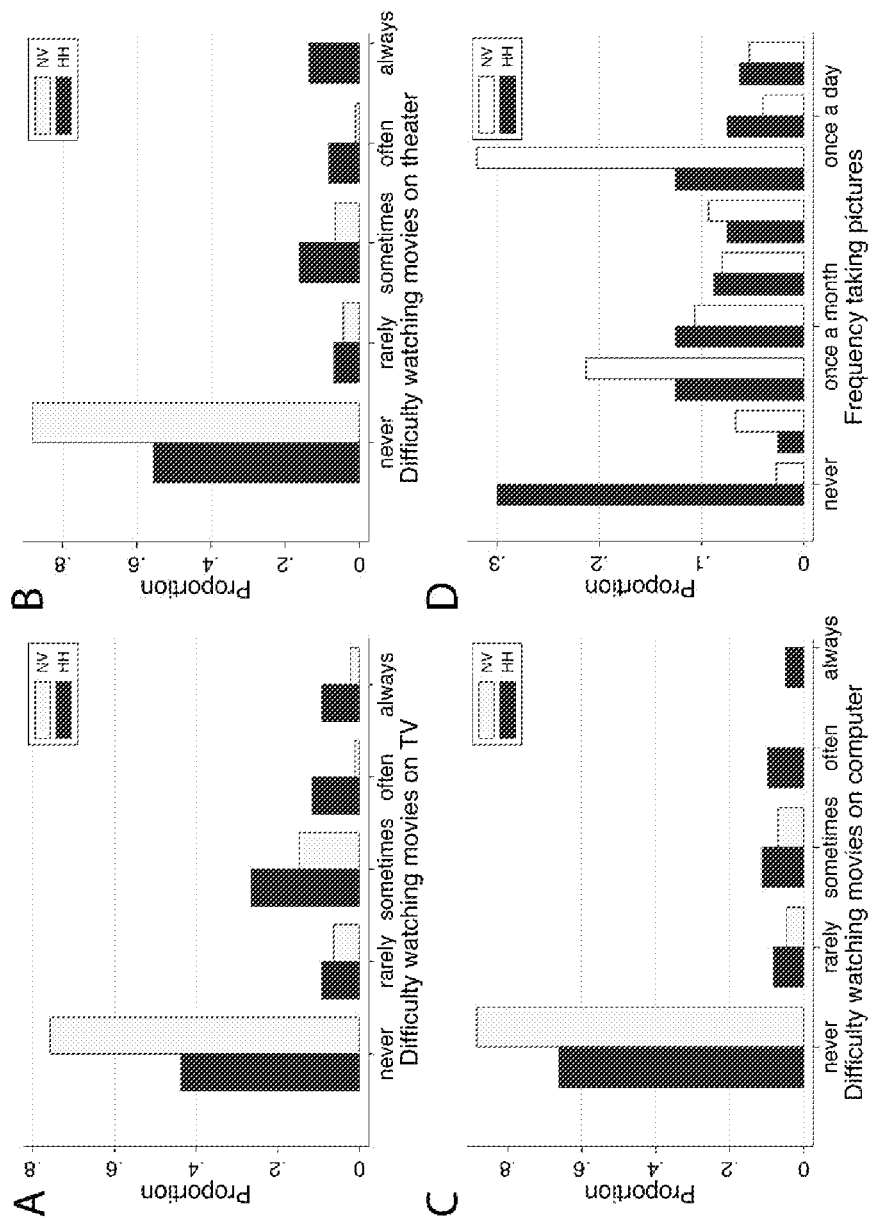
FIG. 3 illustrates questions of the video viewing habits survey where homonymous hemianopia (HH) participants reports were significantly different from normal vision (NV) participants.

For Study 1 the median amount of TV watched per day was 2 to 3 hours and was slightly higher among participants with hemianopia (OLR, p=0.05). The number of hours of TV watching increased with age for people with normal sight (Spearman, rho=0.33, p<0.0001), whereas for participants with hemianopia there was no change with age (rho=0.11, p=0.30). Frequency of viewing reduced with increasing level of education (OLR, z=3.78, p<0.001). Five participants with hemianopia and three with normal vision reported watching no television (zero hours/day). When watching TV, 57% of people reported that their viewing occurred when there was usually no other viewer ('sometimes' or less). Participants with hemianopia were slightly less likely to watch TV with others (OLR, z=1.90, p=0.06) regardless of age (Spearman, rho=0.13, p=0.26) while participants with normal vision decreased the likelihood of watching in the presence of another viewer with increasing age (Spearman, rho=−0.19, p=0.03). Viewing without another person present provides the opportunity to use a rehabilitation aid such as image enhancement that might be unacceptable to a viewer with normal vision. As shown in FIG. 3, participants with hemianopia (56%) were more likely than participants with normal vision (24%) to report at least 'some' difficulty watching TV (OLR, z=4.71, p<0.0001). There was no change with age in reported difficulty watching TV (z=1.15, p=0.25). Participants with hemianopia (30%) were more likely than participants with normal vision (6%) to report the use of a special strategy, assistive device, or visual aid while watching TV or movies (LR, z=3.02, p=0.003). Examples included TiVo (allows going back to review segments), DVR, scanning, telescope, Fresnel prism, and glasses specifically for TV.

Most (184/251) participants reported never using a portable device (e.g. iPhone, personal DVD player) to watch videos, with no difference between the groups (LR, z=1.02, p=0.31). Older participants (LR, z=3.58, p<0.001) and males (LR, z=2.23, p<0.03) were less likely to have watched video on a handheld device. Of the participants who watched video on handheld devices, participants with hemianopia (22/29 reported 'never'), as compared to participants with normal vision (10/22), were less likely to report that they had difficult seeing details (OLR, z=1.94, p=0.05).

Most (86%) participants reported having a computer at home, with no significant difference in availability between the two groups (OLR, z=1.06, p=0.29). Older participants with normal vision were less likely to have a computer at home than younger participants (rho=−0.25, p=0.004) but there was no effect of age among the participants with hemianopia (rho=0.00, p=0.94). Of the participants reported to have a computer at home, only 39% of the NV participants and 29% of the participants with hemianopia watched movies (e.g. DVD) on the computer. Frequency of viewing movies on a computer decreased with increasing age (OLR, z=4.11, p<0.001), with no difference between the two groups (z=0.61, p=0.54). Most participants with internet access (127/191) reported watching internet video content (e.g. YouTube, Hulu, TV shows from network web sites), with no difference between the groups (z=0.16, p=0.88) and frequency declined with increasing age (z=6.74, p<0.001). Among those people watching video material on computer, it was uncommon for there to be another viewer present, with only 23/158 reporting another viewer often or always present, with participants with hemianopia being less likely to have another viewer present (OLR, z=2.30, p=0.02). Among, older participants with normal vision, the likelihood of having another viewer present deceased with age (rho=−0.45, p<0.001), whereas there was no variation with age among the participants with hemianopia (rho=−0.01, p=0.93). Participants with hemianopia (26% at least 'sometimes') were more likely (OLR, z=2.56 p=0.011) to report having difficulty with details on a computer screen than NV participants (7%), with no effect of age (z=0.37, p=0.72). Over a quarter (15/63) of the participants with hemianopia who used a computer reported at least 'sometimes' to use assistive technologies, which was more than the 3% of the NV participants who reported using assistive technologies (z=2.68, p=0.007). Older participants with hemianopia were less likely to use assistive technologies with the computer (rho=−0.25, p=0.004), with no age effect among participants with normal vision (rho=0.03, p=0.85).

TABLE

Summary of video viewing habits compared between the hemianopia group (N = 93) and normally-sighted (NV) group (N = 193). FIG. 6 illustrates a similar table with some additional information.

| (Survey questionnaire number), survey question | NV Mean (range)/ proportion | Hemianopes Mean (range)/ proportion | Statistical test of difference |
|---|---|---|---|
| (1) How many hours do you watch TV? | 2(0-5) | 2(0-6) | D = 0.0390, p = 1 $X^2$(4) = 23.64, p = 0.001 |
| (3) Do you find it difficult when watching movies on the TV? (>never) | 24.2% 23/95 | 56.3% 49/87 | z = 4.71, p < 0.0001 |
| (4) Do you use any special strategy? (yes/no) | 5.7% 3/52 | 30% 24/80 | z = 3.02, p = 0.003 |
| (6) Do you ever watch TV, movies on a portable device? (yes/no) | 24.5% 40/163 | 30.6% 27/88 | z = 1.02, p = 0.31 |
| (8) Do you have a computer at home? (yes/no) | 83.2% 109/131 | 91.3% 74/81 | z = 1.06, p = 0.29 |
| (9) Do you ever watch DVDs on a computer? (>never) | 39.1% 45/115 | 53.3% 40/75 | z = 0.61, p = 0.54 |
| (10) Do you ever watch videos on the internet? (>never) | 68.9% 80/116 | 62.6% 47/75 | z = 0.16, p = 0.88 |
| (12) Do you find it difficult to see details when watching DVDs on a computer? (>never) | 11.6% 5/43 | 30.6% 19/62 | z = 2.56 p = 0.011 |
| (13) Do you use assistive technology on your computer? (>never) | 2.2% 1/44 | 28.5% 18/63 | z = 2.68, p = 0.007 |
| (15) How often do you go to the movie theater? (>never) | 81.2% 134/165 | 65.5% 57/87 | z = 2.80, p = 0.05 |
| (16) Do you find it difficult to see details when watching movies at the theater? (>never) | 11.9% 11/92 | 44.5% 33/74 | z = 4.73, p < 0.001 |
| (18) How often do you take pictures? (>never) | 97.3% 73/75 | 67.5% 54/80 | z = 4.93, p < 0.001 |
| (22) Do you find it difficult to take a good picture? (>never) | 46.7% 35/75 | 51.4% 35/68 | z = 1.33, p = 0.18 |

About 3/4 participants reported watching movies in a theatre (cinema), with most going to the theatre a 'few times a year'. Frequency of attendance decreased with age (OLR, z=3.58, p<0.001) and participants with hemianopia reported lower frequency (z=2.80, p=0.05). In particular, participants with hemianopia (34%) were much more likely (LR, z=3.56, p<0.001) to report never attending the theatre than normal vision (19%). As shown in FIG. 3, participants with hemianopia (28/74) were more likely to report at least 'some' difficulty watching movies in a theatre (OLR, z=4.73, p<0.001) than participants with normal vision (7/92).

As shown in FIG. 3, many participants with hemianopia (24/80) reported never taking photographs, which was more likely than among participants with normal vision (LR, z=4.93, p<0.001). Overall, older participants (OLR, z=4.10, p<0.001), participants with hemianopia (z=2.02, p=0.04), participants with less education (z=2.40, p=0.02) and males (z=1.80, p=0.07) took photographs less frequently. Of those that did take photographs, there was no difference between the groups (z=1.33, p=0.18) or effect of age (z=0.20, p=0.84) in the difficulty taking photographs. Participants with hemianopia who expressed difficulties described problems locating the picture target using the device (28%), understanding the technology (23%), placing the picture target at the desired location in the picture (19%), fitting multiple targets in the picture (16%), and issues related to lighting or focusing (14%). Sharing of photographs was less frequently among older participants (OLR, z=3.28, p<0.001) and participants with less education who had hemianopia (Spearman, rho=0.27, p=0.03) but not for participants with normal vision (rho=0.03, p=0.81).

Compared to people with full sight, people with hemianopia watch as much TV, have more difficulty watching TV, attend movie theater less frequently, have more difficulty watching movie in cinema, and take photographs less frequently.

For study 2 measuring information acquisition, the participants with hemianopia, on average, had an IA score that was 1.54 shared words lower than the normal-vision participants (mixed-effects regression, z=5.38, p<0.001), when corrected for age. Age was significantly related to the IA score (z=4.00, p<0.0001), with IA score decreasing 0.32 shared words per decade. Other co-variates gender (p=0.51), maximum education level (p=0.49), MoCA score (p=0.86), race (p≥0.88) and visual acuity (p=0.82), were not significant in the model. Among the subjects with hemianopia, cause of hemianopia (p≥0.55) and hemianopia side (p=0.33) and measured neglect or history of neglect (p=0.39), were not related to IA score in our sample.

Also investigated were relationships between some of the responses to the survey and IA score. When corrected for age, IA score was not related to hours per day watching television (p=0.50), difficulty watching television (p=0.73)

or video on a computer (p=0.70) or movies at a cinema (p=0.61). Among the normal-vision group, when corrected for age, a higher frequency of attendance at the cinema was associated with a higher IA score (p=0.04), but not among the hemianopic group (p=0.60). Similarly, high frequency of taking photographs was associated with higher IA score among the normal-vision group (z=2.61, p=0.009), but not among the hemianopic group (p=0.68).

Figure 4:
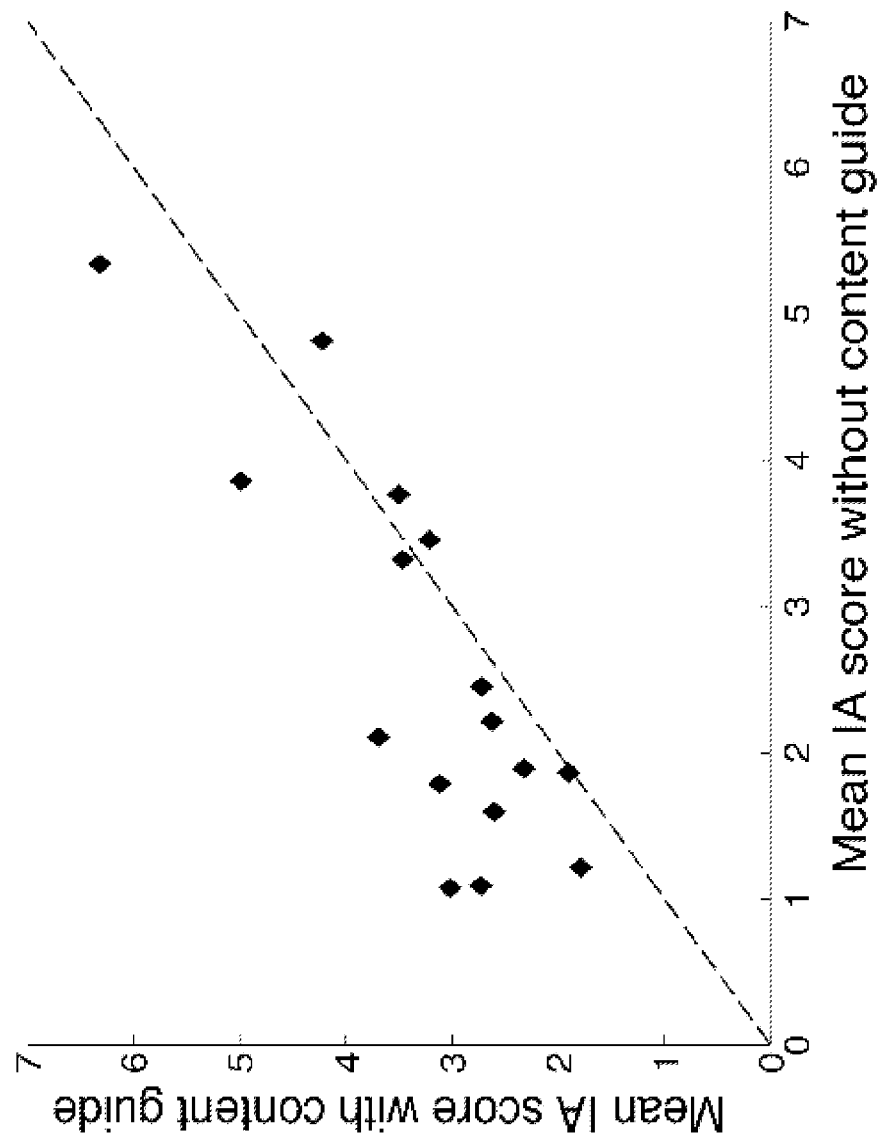
FIG. 4 illustrates results of the study 3 using the content guide. The change in information acquisition resulting from the content guide for each hemianopic participant. Symbols that appear above the dashed line represent participants whose mean information acquisition score improved with the content guide.

For study 3, for the 17 subjects with hemianopia, the content guide improved the IA scores by 0.54 shared words on average (mixed-effects regression, z=4.67, p<0.001) from 2.9 to 3.5 shared words, when corrected for age (p=0.82). No covariates were significant (p≥0.38), including block order (i.e. which condition was seen first; p=0.47). As shown in FIG. 4, mean IA scores were significantly higher for the hemianopia group when the content guide was present for 14 of the 17 participants.

Figure 7:
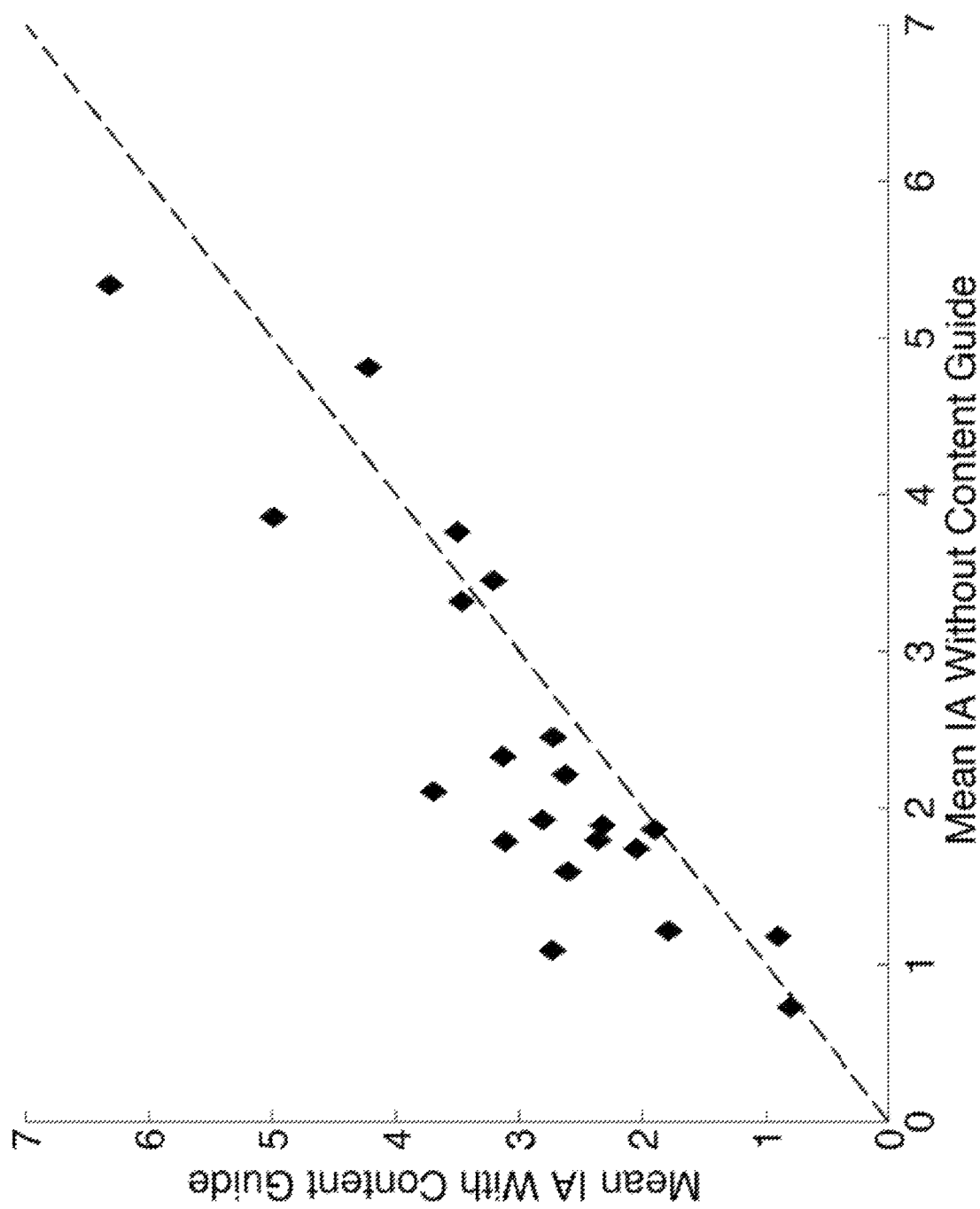
FIG. 7 illustrates results of Study 2 showing the mean IA score with and without the content guide for each participant.

In a similar study, 21 participants with HH watched the thin yellow line centered over the COI. The IA scores were compared between these two viewing conditions. A mixed-model analysis to test for an effect of the fixed factor, "content guide present", since "participant" and "video clip" were fully-crossed random factors. As shown in FIG. 7, presence of the content guide significantly increased the IA score by 0.52 shared words (z=2.28, p=0.023), and was higher in most (17/21) of the participants with HH. Thus, 17 out of 21 hemianopia patients showed improvement in their mean IA score using the enhancement.

A previous, smaller (n=47) survey (Warren, 2009), reported that 30% of participants with hemianopia reported difficulty with "following the action in programs" on television, which is consistent with the 47% who reported at least "sometimes" having difficulty with television in our survey. In the survey, similar difficulties were also found with related activities, and the video-viewing habits of people with hemianopia showed some interesting differences from people with normal vision. The participants with hemianopia reported more difficulty while watching TV (p<0.001), with watching video on a computer (p=0.01), and with watching movies at the theater (p<0.001) (Table 2; FIG. 3). Participants with hemianopia reported watching slightly more television (p=0.05) and were equally as likely to watch video on a hand-held device or computer, but were much less likely to watch movies in a theater (p=0.005) and much less likely to never take photographs (p<0.001). The lower rates of cinema attendance and photography were presumably because they found these tasks more difficult than people with normal sight, and thus suggest that their visual impairment may make them refrain from engaging in these activities.

Age was often a significant co-variate in our survey sample, with the use of a hand-held device to view video (LR, p<0.001), and the frequency of viewing a DVD using a computer (p=−0.35, p<0.001), viewing video content from the internet on a computer (p=−0.53, p<0.001), attending the cinema (p=−0.19, p=0.002), taking photographs (p=−0.40, p<0.001) and of sharing photographs (p=−0.20, p=0.02) decreasing with increasing age in both groups. Older participants with normal vision watched more television (p=−0.32, p<0.001) and were less likely to have a computer at home (p=−0.35, p=0.02), but there was no change with age among the participants with hemianopia (p>0.30). These substantial effects of age on video viewing and computer use is consistent with previous findings (Woods and Satgunam, 2011).

Although self-reported difficulties with activities of daily living, such as watching television, have been previously reported for hemianopia (Warren, 2009), and were confirmed in the survey, this study is the first demonstration that watching video is not only perceived to be more difficult by people with hemianopia, but is more measurably difficult. The objective method (used in Study 2) showed that participants with hemianopia were less able to acquire information. The significant reduction in information acquisition score found in the hemianopia group confirms that there is a systematic problem with the viewing experience of people with hemianopia when watching video content. Therefore, there is a need for visual rehabilitation for video viewing.

The method of presenting a content guide around the COI can be beneficial as it directs hemianopes' gaze towards the most visually informative area of the movie, thus improving their information acquisition. This method was successful in increasing the IA scores in 14 of 17 hemianopes (FIG. 4), probably by reducing the tendency to make scanning eye movements into the blind side. When the guide is in the scotoma, it is not visible. Patients would notice its absence, and that will act as an alert to the presence of a region of interest in the scotoma. The fact that there was a significant improvement is encouragement to pursue the approach of superimposing a guide to the most important areas of the display, continually updated, to help people with hemianopia to view video. In this experiment, neither hemianopic nor control viewers had practice with the content guide before beginning the experimental trials, and so they had to learn how to use it over the course of the experiment. For future tests of the content guide, it is possible to give participants a long practice period to acclimatize to the content guide and to learn to associate it with areas that are particularly informative, while deemphasizing areas of the display that are not seen through the content guide. Compensatory scanning has been proposed as a form of rehabilitation treatment, with some success (Hayes et al., 2012, de Haan et al., 2015). However, during training, it may be important to teach them that different strategies are optimal for different tasks. Superimposing a content guide on video may aid such patients in shifting gaze strategies to the appropriate one for video, and in particular patients who spontaneously develop compensatory eye movement strategies.

There was strong interest in the sample for assistive technology, with half of the participants with hemianopia indicated an interest in assistive technology for watching television (41/80) and for watching video content on a computer (33/64). There was plenty of opportunity, watching with another person only sometimes or less frequently was common with television (45/79) and very common for watching video on a computer (55/63).

Example 3

Hemianopia includes a cortical blindness, most commonly from stroke, that usually eliminates vision on one side in both eyes (homonymous), and thus reducing visuo-spatial perception. This vision impairment diminishes the quality of life and negatively impacts activities of daily living, such as noticing other persons, reading, walking and driving. Another activity that may be severely affected is watching television and other forms of video. A previous survey of 46 people with hemianopia and quadranopia, which included one question about television, found that 30 percent reported some difficulty with watching television. Such difficulties could arise from information missed due to the scotoma, eye movement control including compensatory scanning and reading problems when text is presented. This may lead to difficulty following the story, and a consequent reduction in value from the viewing experience.

The prevalence of homonymous visual field defects has been reported as 0.8% in the general population over 49 years of age. As there were about 100 million people aged 50 years and older in the USA in 2010, this suggests that there were about 800,000 people in the USA with a homonymous visual field defect. The proportion of visual field deficits can be as high as 49% in an acute stroke care setting, though many visual field deficits resolve in one to six months. Of stroke survivors, 8% to 16% have long-term hemianopia, most of which are partial or complete homonymous hemianopia. As there were 6.2 million stroke survivors in the USA in 2010, this suggests that between half and one million stroke survivors in the USA have a permanent hemianopic visual field deficit, which is consistent with the other prevalence estimate above.

Risk of hemianopia increases with age, as does the time watching television. People 65 years and older in the U.S.A. watch over 49 hours of television a week on average. Therefore, it is important to understand the scale of this problem, to investigate its causes, and to develop treatments or aids. Many rehabilitation strategies have been adopted for people with hemianopia, including vision restitution (or restoration), compensation (e.g. scanning training), and substitution (e.g. prisms), with evidence of benefit from some but not all recent randomized trials.

In the USA, hemianopia is not generally considered a vision impairment and people with hemianopia do not usually obtain any government assistance at a Federal or state level. Even so, people with hemianopia are not able to hold a driver's license in many states. The situation differs in other jurisdictions, with hemianopia being considered a vision impairment in some, and thus entitled to forms of assistance. In certain jurisdictions driving is allowed, usually after a driving evaluation. People with hemianopia are often not referred to vision rehabilitation services by primary care, neurology or neuro-ophthalmology. If we presume that hemianopia is worthy of vision rehabilitation efforts, as there are about half as many people with hemianopia (about 0.8 million), as people with central vision loss with VA 20/70 or worse (about 1.5 million), we might expect people with hemianopia to be about 1/3 of the patients in vision rehabilitation clinics, but that has not been our experience, there being much fewer than one would expect.

Here, is reported a systematic survey of people with hemianopia (N=91) that is focused on watching video in various formats, including their viewing habits, the difficulties that they experience, and compensatory strategies that they employ. Items from a previous survey of people with central vision loss were employed. As people with hemianopia had reported difficulties taking photographs to us, our survey also included questions related to their habits taking photographs. We include 192 people with normal vision as a control group.

Materials and Methods: Survey. The viewing-habits survey was similar to a previous survey that investigated the viewing habits of people with impaired central vision. It was administered either in person (n=22) or as a telephone interview (n=69). Verbal consent from each participant was obtained for the telephone-administered survey after the study was explained and the consent form was read out. Written consent was obtained from participants who took the survey in person. In addition to demographic and clinical questions, there were five questions related to television viewing habits, two about portable devices, seven about computer use, two about the cinema and six questions about photography. Data collection was administered by an examiner who recorded verbal responses using a custom computer interface. The viewing-habits survey took about 10 to 15 minutes to complete.

Participants. Of the 283 participants, 192 had normal vision and 91 had some form of hemianopia. These participants were primarily from Massachusetts (111/192 normal vision and 68/91 hemianopia). People with hemianopia came from three sources: (1) people who had participated or expressed a willingness to participate in studies at the Schepens Eye Research Institute (n=79); or (2) had been patients at the Massachusetts Eye and Ear Infirmary, Boston Mass. (n=10); or (3) volunteered in response to advertisements placed on the ResearchMatch.org website (n=2). For the survey, hemianopia was documented as lack of vision by quadrants. So, a participant with hemianopia would have two quadrants with missing vision, except for the two participants with bitemporal hemianopia. Some of the participants did not have complete hemianopia, having some vision beyond the midline, but the majority of the visual field was missing in both quadrants. For the participants seen at the institute, visual fields were measured with a Goldmann perimeter. For participants interviewed by telephone only, some were able to provide visual field measurements, while the rest answered questions about their ability to see in the four quadrants. Participants from Massachusetts Eye and Ear Infirmary were identified using a billing code (ICD-9) for homonymous hemianopia. Potential participants with hemianopia who reported physical disability that might affect their ability to view video were not included. In our survey sample, the reported cause of hemianopia was similar to previous studies, with 61% stroke, 11% traumatic brain injury, 13% a tumor and 11% a consequence of brain surgery.

Participants with normal vision had visual acuity with both eyes of 20/30 or better and self-reported normal vision (using a questionnaire). Some participants with normal vision had visual acuity in one eye that would not be considered normal vision on its own (e.g. 20/200 in the right eye). However, those participants had good visual acuity when viewing with both eyes and full visual fields (e.g. 20/20 for that example participant), so had functionally normal vision (as daily activities are usually conducted with both eyes open). Analyses without these participants with one eye worse than 20/30 did not alter the interpretation of the outcomes reported below.

There were younger (20 to 35 years) and older (75 to 85 years) participants in the normal vision sample (Kolmogorov-Smirnov two-sample, p=0.02). Age was included as a covariate in analyses. There were no differences in education (p=0.23) or gender (p=0.14) between the two groups. The participants with hemianopia were more likely to be white than the normal vision participant group (p=0.003).

Statistical analyses. Data from the FileMaker Pro survey database were exported into the Stata statistical package (version 14, Stata, College Station, Tex.) for data analysis. Comparisons between the hemianopia and control groups for the survey questions used logistic regression and ordered logistic regression as these allowed inclusion of the covariates age, education level, and gender. Since we performed many statistical analyses, $p \leq 0.01$ was considered statistically significant. As our sample size was not large (N=283), effects that approached significance ($0.01 < p \leq 0.10$) are also noted.

Results. Responses of participants with hemianopia were significantly different from participants with normal vision for many items.

Television. The median amount of television watched per day was 2 to 3 hours and was not different between the two groups (ordered logistic regression, z=1.00, p=0.32). As reported previously, the number of hours of television watching increased with age (z=2.83, p=0.005), and that did not vary significantly between the groups (z=0.60, p=0.59). Frequency of viewing reduced with increasing level of education (ordered logistic regression, z=3.64, p<0.001) and tended to be more for male participants (z=1.76, p=0.08). Four participants with hemianopia and three with normal vision reported watching no television (zero hours/day). When watching television, 58% of people reported that their viewing occurred when there was usually no other viewer ('sometimes' or less). Participants with hemianopia were slightly less likely to watch television with others (ordered logistic regression, z=1.90, p=0.03), regardless of age (z=1.31, p=0.19). Conversely, participants with normal vision decreased the likelihood of watching in the presence of another viewer with increasing age (z=−2.46, p=0.01). Participants with hemianopia (58%) were more likely than participants with normal vision (18%) to report at least 'some' difficulty watching television (ordered logistic regression, z=4.57, p<0.0001). There was no change with age in reported difficulty watching television (z=0.91, p=0.36). Comments about the experienced difficulties included not seeing things of interest on the blind side, difficulty with specific viewing situations (e.g. following ball path to right handed batter in baseball; tennis; fast action) and with text, particularly scrolling text. Participants with hemianopia (30%) were more likely than participants with normal vision (6%) to report the use of a special strategy, assistive device, or visual aid while watching television or movies (logistic regression, z=3.12, p=0.003). The 24 participants with hemianopia who reported as assistive strategy for watching television reported (numbers add to >24, as some participants reported more than one strategy): only watching with a spouse who could assist with understanding (n=2), using a video storage device such as a DVR or TiVo (allows going back to review segments, n=4), compensatory scanning (n=3), glasses specifically for television (n=3), closing one eye (n=2), tilting the head (n=2), turning the head or looking to the side (n=3), sitting to one side (n=4), and using closed captions (n=2). Six reported using peripheral prism glasses and one reported that they did not help for viewing television. This survey was not able to assess whether these approaches provided real benefit, and it was not obvious to us how some of the reported strategies might help. We presume that a viewer would only continue with the use of a strategy if it was perceived to provide a benefit to them.

Portable devices. Most (73%) participants reported never using a portable device (e.g. iPhone, personal DVD player) to watch videos, with no difference between the groups (logistic regression, z=0.74, p=0.46). Older participants (z=4.08, p<0.001) and females (z=1.94, p=0.05) were less likely to have watched video on a handheld device. Of the 51 participants who reported watching video on handheld devices, there was a tendency for participants with hemianopia (22/29 reported 'never'), as compared to participants with normal vision (10/22), to be less likely to report that they had difficult seeing details (ordered logistic regression, z=1.94, p=0.05). It is possible that this outcome was a result of selection bias, with only those with hemianopia who were able to use a portable device to view video providing a response about difficulty.

Computer. Most (86%) participants reported having a computer at home, with no significant difference in availability between the two groups (ordered logistic regression, z=1.06, p=0.29). Older participants with normal vision were less likely to have a computer at home than younger participants (z=2.45, p=0.01) but there was no effect of age among the participants with hemianopia (z=0.13, p=0.90). Of the participants reported to have a computer at home, only 39% of the normal vision participants and 30% of the participants with hemianopia watched movies (e.g. DVD) on the computer. Frequency of viewing movies on a computer decreased with increasing age (ordered logistic regression, z=4.11, p<0.001), with no difference between the two groups (z=0.61, p=0.54). Most participants with internet access (127/191) reported watching internet video content (e.g. YouTube, Hulu, television shows from network websites), with no difference between the groups (z=0.16, p=0.88) and frequency declined with increasing age (z=6.74, p<0.001). Among those people watching video material on computer, it was uncommon for there to be another viewer present, with only 23/157 reporting another viewer often or always present, with participants with hemianopia tended to be less likely to have another viewer present (ordered logistic regression, z=2.30, p=0.02). Among participants with normal vision, the likelihood of having another viewer present deceased with age (z=4.07, p<0.001), whereas there was no variation with age among the participants with hemianopia (z=0.12, p=0.91). Participants with hemianopia (26% at least 'sometimes') were more likely (ordered logistic regression, z=2.56 p=0.01) to report having difficulty with details on a computer screen than normal vision participants (7%), with no effect of age (z=0.37, p=0.72). Over a quarter (14/62) of the participants with hemianopia who used a computer reported at least 'sometimes' to use assistive technologies, which was more than the 2% of the normal vision participants who reported using assistive technologies (z=2.32, p=0.02). Older participants tended to be less likely to use assistive technologies with the computer (z=1.93, p=0.05). The reported assistive approaches were reducing viewing distance (n=3), increasing mouse icon visibility (n=3), large font size (n=2), zoom software (n=2) and reading software (n=1).

Cinema. About 3/4 participants reported watching movies in a cinema, with most going to movie theatres a 'few times a year'. Frequency of attendance decreased with age (ordered logistic regression, z=3.48, p<0.001) and participants with hemianopia reported lower frequency (z=2.80, p=0.05). In particular, participants with hemianopia (34%) were much more likely (logistic regression, z=3.56, p<0.001) to report never attending the cinema than normal vision (19%). Participants with hemianopia (31/72) were more likely to report at least 'some' difficulty watching movies in a cinema (ordered logistic regression, z=4.73, p<0.001) than participants with normal vision (7/92). Turning the head (n=2), sitting to one side (n=3), compensatory scanning (n=2) and peripheral prism glasses (n=1) were reported as strategies to improve the viewing experience. Reasons for never or very infrequently attending the cinema or difficulties when attending included reports of missing information (n=4) or missing objects on the blind side (n=2) making it difficult to follow the story, the very large cinema screen (n=4), fast action (n=4) or reading text on the screen (n=2) and uncertainty about being able to obtain a preferred seating location (to the back so that the screen subtends a smaller visual angle or on the blind side of the cinema, so that the screen is on the seeing side).

Photography. Many participants with hemianopia (24/80) reported never taking photographs, which was more likely than among participants with normal vision (logistic regression, z=4.93, p<0.001). Overall, participants who had hemianopia (ordered logistic regression, z=2.02, p=0.04), were older (z=4.10, p<0.001), had less education (z=2.40, p=0.02) and were male (z=1.80, p=0.07) took photographs less frequently. Of those that did take photographs, there was no difference between the groups (z=1.33, p=0.18) nor an effect of age (z=0.20, p=0.84) in the difficulty taking photographs (note that this subset was biased, as those that had most difficulty did not take photographs). Participants with hemianopia who expressed difficulties described problems locating the picture target using the device (14%), understanding the technology (20%), placing the picture target at the desired location in the picture (9%), fitting multiple targets in the picture (7%), and issues related to lighting or focusing (18%). Some participants with hemianopia reported not taking photographs because of cognitive problems (e.g. cannot find camera, difficulty operating the camera), physical problems (e.g. tremor) and because others take the photographs instead (or take better photographs). Sharing of photographs was less frequently among older participants (OLR, z=3.24, p=0.001) and participants with less education (z=2.55, p=0.01), and did not vary between the two groups (z=0.00, p=1.0).

Reduction in Ability (Information Acquisition) with Hemianopia and the Impact of the Content Guide Most (56%) of the participants with hemianopia reported at least 'some' difficulty watching television, which was much higher than among participants with normal vision. Similarly, a previous, smaller survey[10] reported that 30% of participants with hemianopia reported difficulty with "following the action in programs" on television. In our survey, similar difficulties were also reported with related activities, watching video on a computer and movies at the cinema. Participants with hemianopia were much less likely to watch movies in a cinema and much less likely to ever take photographs. The lower rates of cinema attendance and photography were presumably because they found these tasks more difficult than people with normal vision, and thus suggest that their vision impairment may make them refrain from engaging in these activities. While the difficulties leading to this reduced activity may not be all visual, and could be from other factors such as cognitive or physical impairment, this population has reduced engagement in these activities. Conversely, despite reporting more difficulty watching television, participants with hemianopia reported watching slightly more television. Perhaps this reflects a reduction in other activities due to the vision impairment, and that additional available time is used to watch television, as it is an easy option.

Given the estimate of 500,000 to 1,000,000 people with hemianopia in the USA, our survey was representative of that population and the data suggest that between 280,000 and 560,000 people with hemianopia in the USA feel that they have difficulty watching television. Although self-reported difficulties with activities of daily living, such as watching television, have been previously reported for hemianopia, there have been no assessment methods to measure this difficulty. In a separate study, we provide a demonstration that watching video is measurably more difficult for people with hemianopia, using a recently developed method we call sensory information acquisition. There, information acquisition is a measure of the ability to follow the story. Even when watching video for enjoyment, if you cannot follow the story, the value of the activity is usually diminished.

Half of the participants with hemianopia expressed strong interest in assistive technology. One of the concerns with an intervention that modifies the displayed image is that it may be unacceptable to other viewers watching the same display. Most participants with hemianopia watched television with others infrequently (44/78, sometimes or less). Viewing without another person present provides the opportunity to use a rehabilitation aid that might be unacceptable to a viewer with normal vision. Participants with hemianopia reported that watching television or video on a computer while alone was common, and, in a previous, related study, the median number of televisions per home was found to be two. People with hemianopia reported a variety of assistive methods (e.g., DVR). In a separate study, we investigated a rehabilitation method that was shown to improve the ability to follow the story (improved information acquisition). The approach involves providing a visual content guide to the location that contains most information. It is sufficient to look at this highlighted region to follow the story. The rationale being that the viewer no longer has to look into the blind side to check whether there are objects of interest (compensatory scanning) and that looking away from the region of interest to make a compensatory scan disrupts the ability to follow the story. If the highlighted region was not visible, then the viewer would know that region of interest was on the blind side and make a gaze shift to locate the highlighted region of interest. Viewers with hemianopia tend to follow the dynamic content guide, so do not lose it into the blind side.

Central vision loss (reduced visual acuity) is the most common form of low vision. Reported here are differences and similarities in the responses of 116 participants with central vision loss (visual acuity of 20/60 or worse), most of whom participated in a previous study, to our participants with hemianopia. Participants with central vision loss reported similar frequency of television viewing (z=0.15, p=0.88), more difficulty watching television (z=8.35, p<0.001), less use of assistive strategies (z=1.99, p=0.05), but more interest in enhancement technologies for television and movies (z=6.73, p<0.001). Participants with central vision loss tended to be less likely to have a computer at home when corrected for age (z=1.87, p=0.06), were as likely to watch movies on a computer (z=0.96, p=0.34) or use the internet (z=0.93, p=0.35), reported more difficulty viewing movies and video on a computer (z=4.92, p<0.001), were more likely to report using an assistive technology when using the computer (z=3.65, p<0.001), and were more likely to be interested in enhancement technologies for use when watching movies and videos using the computer (z=6.93, p<0.001). Overall, participants with central vision loss had a similar frequency of cinema attendance (z=1.41, p=0.16), though tended to be less likely to never attend (z=1.65, p=0.10).

This survey found that participants with hemianopia report difficulties watching video in various formats, including television, on computers and in a movie theater. While these reported difficulties were not as marked as those reported by people with central visual loss, the reported difficulties were greater than those reported by participants with normal vision. These difficulties seem to lead to reduced attendance at movie theaters and reduced taking of photographs. These changes in behavior and difficulties with activities of daily living are related to a reduced quality of life experienced by people with hemianopia that may not be well captured by various instruments.

Example 4: Measuring the Difficulty Watching Video with Hemianopia and an Initial Test of a Rehabilitation Approach If you cannot follow the story when watching a video, then the viewing experience is degraded. We therefore measured the difficulty following the story, the ability to acquire visual information, experienced by people with homonymous hemianopia (HH). Further, we proposed and tested a rehabilitation aid.

Participants watched 30-second directed video clips. Following each video clip, subjects described the visual content of the clip. An objective score of information acquisition (IA) was derived by comparing each new response to a control database of descriptions of the same clip using natural-language processing. Study 1 compared 60 participants with normal vision (NV) to 24 participants with HH to determine whether participants with HH would score lower than NV participants, consistent with reports from people with HH that describe difficulties in video watching. In the second study, 21 participants with HH viewed clips with or without a superimposed dynamic cue that we called a content guide. We hypothesized that IA scores would increase using this content guide.

The HH group had a significantly lower IA score, with an average of 2.8, compared to 4.3 shared words of the NV group (mixed-effects regression, p<0.001). Presence of the content guide significantly increased the IA score by 0.5 shared words (p=0.03).

Participants with HH had more difficulty acquiring information from a video, which was objectively demonstrated (reduced IA score). The content guide improved information acquisition, but not to the level of people with NV.

As discussed above, HH is a cortical blindness that eliminates vision on one side in both eyes. The prevalence of homonymous visual field defects has been reported as 0.8% in the general population over 49 years of age. As there were about 100 million people aged 50 years and older in the USA in 2010, this suggests that there are over 800,000 people in the USA with a homonymous visual field defect. In an acute stroke care setting, the proportion of visual field deficits can be as high as 49%, though many visual field deficits resolve in one to six months. Of stroke survivors, 8% to 16% have long-term hemianopia, most of which are partial or complete homonymous hemianopia. As there were 6.2 million stroke survivors in the USA in 2010, this suggests that between half and one million stroke survivors in the USA have a permanent hemianopic visual field deficit.

The vision impairment from HH often reduces the quality of life, impacting daily life activities, such as noticing other persons, reading, walking, driving, and watching TV and other forms of video. A survey of 46 people with hemianopia and quadranopia, which included one question about television, found that 30% reported some difficulty with watching television. In a more extensive study of viewing habits, the experience of 91 people with hemianopia with various forms of video access (e.g. television, theater) was compared to that of 192 people with normal vision (NV). Participants with hemianopia were more likely to report difficulty watching TV, movies on a computer, and movies at the cinema, and were less likely to attend the cinema.

With age, the risk of hemianopia increases, as does time watching TV; over 49 hours a week on average for people 65 years and older in the U.S.A. Despite being more likely to report difficulty watching television, people with hemianopia watch similar hours of television per day compared to people with NV. Many rehabilitation strategies have been adopted for people with HH, including vision restitution (or restoration), compensation (e.g. scanning training), and substitution (e.g. prisms), with evidence of benefit from some but not all recent randomized trials.

We objectively measured the information acquisition (IA) of participants with HH (N=24) and with NV (N=60). As used here, IA measures the ability to follow the story, which is a primary requirement of watching videos, even when done for pleasure. Studies were carried out to determine whether participants with HH would score lower than NV participants, based on the difficulties that they report while watching video. The second study was an initial test of a novel rehabilitation aid, which was termed "content guide." The content guide serves as an assistive technology as well as a treatment.

Materials and Methods. Information Acquisition (IA) method. IA is an objective measure of the ability to perceive and understand a sensory stimulus, using descriptions of the stimulus made by the observer. In the case of video, IA measures the ability to follow the story. We restricted responses to descriptions of the visual content, even though audio content was available. We have found that, with careful instruction, responses can be restricted to the visual content, with no difference in IA when the audio content is not available. Participants viewed 30-second video clips wearing their habitual optical correction. An experimenter gave the instructions and was in the room during data collection, but the MATLAB program automatically displayed the prompts after viewing each clip, asking the participant to provide verbal responses to the open-ended queries: "Describe this movie clip in a few sentences, as if to someone who has not seen it," and then, "List several additional visual details that you might not mention in describing the clip to someone who has not seen it." Participants were instructed to report, without time constrains, on the visual aspects of the clip only. The spoken responses to each prompt were recorded using a headset microphone and later transcribed.

Video clips. There were 200 video clips, chosen to represent a range of genres and types of depicted activities. The genres included nature documentaries (e.g., BBC's Deep Blue, The March of the Penguins), cartoons (e.g., Shrek, Mulan), and dramas (e.g., Shakespeare in Love, Pay it Forward). The clips were 30 seconds in duration and were selected from parts of the films that had relatively few scene cuts, which was reflected in the average number of cuts per minute in our clips being 9, as compared to approximately 12 per minute in contemporary films. Videos with very fast action are much more challenging for gaze tracking and for enhancement methods that make use of the region of interest. The clips included conversations, indoor and outdoor scenes, action sequences, and wordless scenes where the relevant content was primarily the facial expressions and body language of one or more actors. Participants viewed the clips on a 27-inch display (aspect ratio 16:9) from a 100 cm distance, so the videos were 33° of visual angle wide. The clips were displayed by a MATLAB program using the Psychophysics Toolbox and Video Toolbox. Participants with HH viewed the same set of 20 video clips. Each participant with NV viewed a different set of 40 clips from our set of 200 video clips that included the 20 video clips viewed by the participants with HH. By doing this, each clip was watched by at least 12 of the 60 participants with NV, providing gaze data to obtain the region of interest (see section "Center of Interest (COI) determination" below) and descriptions of the clip (responses) for the control ("crowd") response database to which the new response was compared (see section "scoring of description of the video clips" below). The analysis in study 1 for the NV group included all 40 clips watched by each participant. A further 99 participants with NV viewed the 200 video clips online provided an additional 20 responses per video clip, for a total of at least 32 responses per video clip in the crowd response database.

Processing of audio files. The spoken responses to each prompt were recorded using a headset microphone and later transcribed using MacSpeech Scribe Pro (Nuance Communications, Burlington, Mass., USA) to produce a preliminary transcript, and then a group of online participants verified and corrected the preliminary transcript via Amazon Mechanical Turk, a crowdsourcing internet marketplace enabling individuals and businesses to coordinate the use of human intelligence to perform tasks that computers are currently unable to do.

Scoring of descriptions of the video clips. These natural-language, open-ended responses were automatically scored for their relevant content using a "wisdom of the crowd" approach (e.g., collective opinion of a group of individuals rather than that of a single expert) to determine the IA score. We processed the text of responses with the Text to Matrix Generator toolbox for MATLAB (as described). Each response was compared to each of the responses to the same video clip in a database of responses from 159 participants with NV (including responses from the crowdsourcing participants as well as responses from the 60 NV participants in study 1). There were at least 32 responses per video clip in the response database. Each new response was compared to each of the responses to the same video clip within the response database. The number of words that two responses shared (after removing stopwords), disregarding repeated instances of the word in either response, produced a shared-word count for each pair of responses. The IA score for each video clip for each study participant was the average of the shared-word counts from the paired comparisons with each of the responses from the response database for the same clip. For participants within the NV group, we removed their own response to a given clip from the control dataset when calculating the IA scores ("leave one out" approach).

Study 1: Effect of Hemianopia on Information Acquisition from Video. To investigate the impact of HH on IA, we compared the IA scores of 24 participants with HH to those of 60 participants with NV.

Participants. Participants were recruited from the community in and around Boston, Mass., using contact lists, physician referrals, and former study participant lists. As shown in Table 1, there were 24 participants with homonymous hemianopia, of whom 13 had their blind hemifield on the left side, five were female, and the median age was 61 years (range 19-81 years). For all participants with HH, there was no projection of sight of more than 10 degrees into the blind hemifield within the central 30 degrees. Six participants showed evidence of hemispatial neglect (bells and line bisection tests) and a further three had a previous history of neglect. All six participants with measured neglect showed mild neglect. The cause of the hemianopia was due to a stroke not during surgery for 15 participants (62%; five ischemic, two hemorrhagic, and eight unknown), a stroke during surgery for two participants (8%), traumatic brain injury for four participants (17%), and a brain tumor for three participants (13%). The cause of HH in this sample was similar to previous studies. One of the participants with hemianopia also had glaucoma, but there was no absolute scotoma associated with glaucoma (also participated in Study 2). None of these 24 participants with HH had expressive aphasia and were able to hold a conversation and name objects, so there was no evidence of agrammatism, anomia, or articulation difficulties.

Sixty people with no ocular conditions in self-reported ophthalmic history, no visual field defects (Goldmann perimeter), normal appearance of the retina (Nidek MP-1), and binocular visual acuity better than 20/35 constituted the NV group. The median age of this group was 66 (range 23-87) years and 30 were male. There were no known neurological disorders or evidence of any speech or memory problems among the NV group, apart from one participant who reported having had a stroke nine years before. Her speech was clear and fluent, though a little slower than average.

Visual acuity for all participants was measured while wearing their habitual optical correction at a distance of 6 m. Though the video viewing distance was 1 m, it is unlikely that the focal difference would make a substantive difference. A reduction of visual acuity to 20/50, did not reduce IA scores in a group of 20 NV subjects.

TABLE

Self-reported demographic, clinical, and visual characteristics of all participants (N = 84). TBI = traumatic brain injury. Significance shows the two-sample Kolmogorov-Smirnov test for equality of the distributions between the groups for ordered data (age, education level, visual acuity, MoCA) or the chi-square test for categorical data (gender, race).

|  |  | NV | HH | significance |
|---|---|---|---|---|
| N |  | 60 | 24 |  |
| Gender | Male | 30 | 19 | p = 0.014 |
|  | Female | 30 | 5 |  |
| Duration of HH (median, range) |  | N/A | 11.2 (0.3-55.2) years |  |
| Race | Asian | 1 | 0 | p = 0.17 |
|  | black | 5 | 0 |  |
|  | white | 53 | 23 |  |
|  | white and Pacific Islander | 0 | 1 |  |
| Age (median, range) |  | 66 (23-87) years | 61 (19-81) years | p = 0.35 |
| Education level | <high school | 0 | 0 | P = 0.004 |
|  | High school | 5 | 6 |  |
|  | Some college | 6 | 6 |  |
|  | Technical | 1 | 3 |  |
|  | Associate | 21 | 6 |  |
|  | Bachelor's | 17 | 3 |  |
|  | Master's | 5 | 0 |  |
|  | Professional | 5 | 0 |  |
|  | Doctoral | 5 | 0 |  |
| Visual Acuity Both Eyes at 6 m (median, min-max) |  | 20/20 (20/15 - 20/35) | 20/20 (20/15 - 20/30) | p = 0.45 |
| MoCA score (median, range) |  | 26 (22-30) | 25 (20-30) | p = 0.09 |
| Vision Loss | Right hemi | N/A | 11 |  |
|  | Left hemi |  | 13 |  |
| Cause of HH | Stroke |  | 15 |  |
|  | TBI |  | 4 |  |
|  | Tumor |  | 3 |  |
|  | Surgery |  | 2 |  |

All participants, NV and HH, had a Montreal Cognitive Assessment score above 20, indicating no evidence of substantial cognitive deficits that would interfere with information processing or language production. Compared to the NV group, the HH group had a higher proportion of males (chi-square, p=0.014), a lower maximum education (Mann-Whitney, z=3.7, p<0.001), and there were no differences in age (Kolmogorov-Smirnov, p=0.35), race (chi-square, p=0.17), or visual acuity (Kolmogorov-Smirnov, p=0.45). For MOCA scores there was a tendency for a difference between the two groups (shape of distribution: Kolmogorov-Smirnov p=0.09), but the medians were not different (Mann-Whitney, z=1.58, p=0.12). Informed consent was obtained from each participant prior to data collection. Participants were shown the video clips wearing habitual, not necessarily optimal, optical correction.

Gaze was tracked while watching the video clips.

Study 2: Effect of the Content Guide on Information Acquisition from Video by People with Hemianopia.

People with hemianopia miss, completely or partially, information on one side of the object to which they are attending. So, if a region of interest appears on that blind side, they are not aware of its presence, unless they look in that direction. To reduce the risk of missing important information (e.g. an object with which they might collide), people with HH often use compensatory scanning, eye movements towards their blind hemifield, to provide information from that side. This strategy is taught in rehabilitation programs and can provide benefit to people with HH during certain tasks. Some people with HH develop this compensatory strategy without training, and many do it in an apparently automatic manner.

However, these scans may result in less time attending to the most informative areas in videos found with most commercial films and TV, which could lower information acquisition. The scans may interfere with the ability to follow the story. The content guide highlights the objects of interest, which are highly informative as determined by the gaze patterns of NV viewers. The guide eliminates the need to make compensatory scanning eye movements towards the blind side (made to check whether there are objects of interest), unless participants are trying to find the content guide, which fell onto the blind side.

Center of Interest (COI) determination. To determine objects of interest in each video clip, we found the COI by tracking the gaze of viewers with normal vision using an EyeLink 1000 system (SR Research Ltd., Mississauga, Ontario, Canada). At least 12 of 60 participants with normal vision watched each video clip. We removed saccades and blinks from the data and defined the smoothed median gaze location for each video frame as the COI. First, the median gaze location was calculated from all the gazes for a given frame. Then a smooth function was run through the median gaze location to reduce visual jitter across frames. A kernel density estimate of the fixation points for one frame is shown in FIG. 2A.

Content guide. For this early-stage study, we presented a thin yellow ring centered over the COI (FIG. 2B) in the first or second of two blocks (20 clips per block, with clips and blocks randomly and evenly distributed). Participants were told that the highlighted region in the content-guide condition would identify the objects of most interest, but were not told to look there. IA scores were compared between the two viewing conditions (presence or absence of the content guide).

Participants. All participants with HH from Study 1 also participated in Study 2, except for three participants that could not finish the study due to personal reasons, totaling twenty-one participants. For ten of the participants, the blind hemifield was the left side, five were female, and the median age was 61 years (range 20 to 81) years. Five participants showed evidence of hemispatial neglect and two others had a previous history of neglect. The cause of the HH was a stroke not during surgery for 14 participants (five ischemic, two hemorrhagic, and seven unknown), a stroke during surgery for two participants, traumatic brain injury for three participants, and a brain tumor for two participants.

Statistical analyses. We compared demographics between the groups by applying the two-sample Kolmogorov-Smirnov test for equality of ordered distributions and the chi-square test for categories. Where a difference between groups was noted for an ordered demographic variable, we used the Mann-Whitney test which compares the central tendency of the two distributions. To compare IA scores between groups (with and without HH; Study 1), and the effect of the content guide (IA scores within subjects using the content guide or not, Study 2), we used mixed-effects regression analyses with participant and video clip as crossed-random factors, and gender, age, race, education level, visual acuity, cause of HH, side of HH, and MOCA score as covariates. The random effects account for differences between responses to clips (some clips have higher shared-word scores than others) and differences between responses from participants (some subjects are more articulate than others), removing those sources of variance. Weak effects of gender, age and education level have been found in some groups of participants with NV. Race and cognitive status (MoCA) could affect the form of responses and visual acuity might affect the ability to see details. Non-significant terms (p>0.10) were removed from models in a stepwise manner. Covariates are only reported when the covariate was significant. For example, if MOCA score was not a significant covariate in an analysis, then it was not included in the final model. Block order and neglect (measured or history) were included as fixed factors, and an interaction between neglect and content guide was included in the analysis of the content guide. As the sample sizes were small, we accepted p<0.01 as significant, and report terms with 0.10≤p<0.01 as trends. Analyses were conducted using Stata (version 14, StataCorp LP, College Station, Tex.).

Figure 2:
FIG. 2 illustrates the content guide dynamically directing attention to areas that were fixated by the majority of normally-sighted viewers. A) Kernel density estimate of the gaze points for this particular frame, which is one measure of the region of interest. B) Illustration of a content guide as it appeared for a particular frame of a video clip in the hemianopia study 3.

Results. Study 1: Information Acquisition. The HH group (2.8 shared words, 95% confidence interval 2.3 to 3.3) had an IA score that was 1.5 shared words lower than the NV participants (4.3 shared words, 95% confidence interval 4.0 to 4.6), when corrected for age (mixed-effects regression, z=5.69, p<0.001; FIG. 2).

Figure 9:
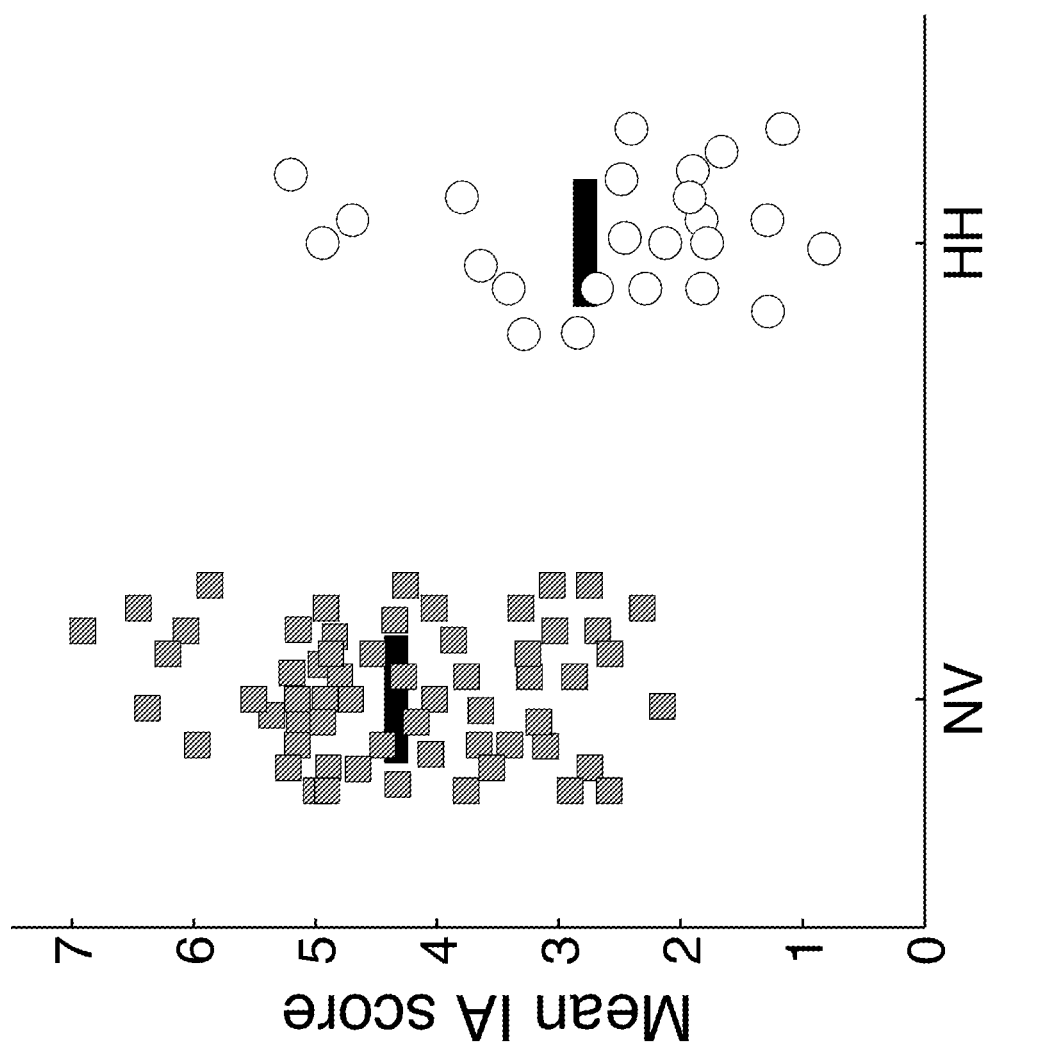
FIG. 9 illustrates a mean IA score for each group according to a study. Dark squares represent normal vision participants (N=60) while white circles show homonymous hemianopia participants (N=24). Flat horizontal black lines correspond to the average for each group.

FIG. 9 illustrates a mean IA score for each group. Dark squares represent NV participants (N=60) while white circles show HH participants (N=24). Flat horizontal black lines correspond to the average for each group.

Age was significantly related to the IA score (z=3.49, p<0.001), with IA score decreasing 0.24 shared-words per decade. Other co-variates, such as gender, maximum education level, MoCA score, race, duration of hemianopia and visual acuity, were not significant (p>0.35), and therefore were not included in the final model. Among the participants with HH, measured neglect or history of neglect (z=0.42, p=0.67) and cause of HH (z<0.30, p>0.76), were not related to IA score in our sample. There was a trend for subjects with right HH to have a lower IA score (−0.80 shared words, z=1.62, p=0.10).

Study 2: Content Guide. For the 21 participants with HH, the content guide improved the IA scores by 0.5 shared words on average (mixed-effects regression, z=2.18, p=0.03) from 2.5 (95% confidence interval 1.8 to 3.0) shared words without guide to 3.0 (95% confidence interval 2.3 to 3.5) shared words with guide, when corrected for gender. In this sample, males had 1.0 shared words less than females (z=1.85, p=0.065). Except for gender, no covariates were significant (p>0.46), including presence or history of neglect (p=0.92) and block order (i.e. which condition was seen first;

p=0.84). There was no difference in the effect of the content guide between the participants with and without neglect (z=1.09, p=0.27). The improvement of 0.5 shared words is a Cohen's d (effect size) of 0.29, which is considered small to medium. Mean IA scores were higher when the content guide was present for 17 of the 21 participants.

When there was a scene cut, the content guide had to relocate to a new COI (that changed instantaneously with the scene cut). When this occurs, a viewer with normal vision will quickly make a saccade to the new COI. Since the content guide followed the COI as defined by the group of viewers with normal vision, the content guide would move following a scene cut. That move was not as fast as a saccade, since the NV viewers would make their relocation saccades at slightly different times and we restricted how quickly the content guide could move. Even so, it is possible that having more scene cuts might affect the ability to follow the story and the value of the content guide. When viewing original clips, there was no effect of the number of scene cuts on the IA score in the NV group (z=0.08, p=0.93). For the HH group, there was no effect of the number of scene cuts on the IA score when viewing original clips (z=0.16, p=0.87) and this did not change when viewing the content guide (z=0.45, p=0.66).

FIG. 7 illustrates results of Study 2 showing the mean IA score with and without the content guide for each participant with HH. Markers that appear above the dashed line represent participants whose mean IA score improved with the content guide.

Self-reported difficulties with watching television, an activity of daily living, have been previously reported for hemianopia. As the prevalence of hemianopia in the USA is estimated to affect 0.5 to 1 million people, and difficulty watching television is reported by 30% to 56% of the people with hemianopia, this suggests that between 150,000 and 560,000 people with hemianopia in the USA feel that they have difficulty watching TV because of hemianopia. Study 1 is the first demonstration that watching a video is measurably more difficult for people with hemianopia. The reduction in IA score among people with hemianopia is as great as that experienced by people with central vision loss.

Study 2 investigated our method of presenting a content guide around the COI. Our approach guided the viewer's gaze towards the most visually informative area of the movie, and was found to improve their information acquisition (IA score). While we found no effect of block order, the improvement in IA could be due to a placebo effect, with the participants noting the intervention (yellow ring at the COI) and trying harder in those trials. We did not tell the participants that this would improve their viewing experience, nor did we ask that they look at the ring, instead, we told the participants that things of interest were highlighted by the ring and allowed them to decide how to make use of it. To fully assess the content guide, we propose a randomized controlled trial in which, for one condition, the content guide will follow a path that is not associated with the clip (i.e. different from the democratic COI for the clip) as a control for a placebo effect from content-guide presence, besides the already existing control condition with no content guide.

In our study, participants were told that the highlighted region in the content-guide condition would identify the objects of most interest, but were not told to look there. If the content guide was not visible, they understood that it could be located by making an eye movement (scan) into the blind side (the scotoma). The viewer knows that the content guide is the region with most of the important information. Therefore, making compensatory scans into the blind side to check for important content that might be missed due to the scotoma is no longer required. This compensatory scanning is a widely used form of rehabilitation treatment that has been shown to improve performance on certain tasks. The intention of the content guide is not to train users not to make compensatory scans, nor is it expected that using the content guide will cause a reduction in compensatory scans in other settings.

The rationale for the value of the content guide is that compensatory scanning may take attention away from the most informative region (the COI) in a video, and thus these scans may impair the ability to follow a video storyline. Thus, the benefit from the content guide may come both by drawing attention to the most informative region and by the reduction of scans into the blind side. We are examining this hypothesis separately by measuring whether there was a decrease in compensatory scans when viewing video clips with the content guide.

To put the average 0.52 shared words increase in IA scores with the content guide in context, we evaluated the variability of IA scores by comparing the score obtained with the first 20 video clips to that obtained with the second 20 video clips, of the 40 clips seen by the 60 participants in the NV group. While not an ideal evaluation of test-retest repeatability, it provides some estimate of variability in the metric. The repeatability coefficient (95% confidence interval) was ±1 shared word. Thus, the improvement was less than the within-session variability that might be expected. Further, the average IA score of 3.0 shared words with the content guide was still substantially less than the NV group (average 4.3 shared words). Thus, while this preliminary study showed that the content guide provided some improvement, it did not bring IA ability of people with HH up to the level of people with NV.

After the completion of the study we did not ask participants whether they preferred using the content guide or if they noticed an improvement in their ability to interpret videos. It is possible that a lack of experience with the content guide limited the value from the content guide in our study. For future evaluations of the content guide, we intend to give participants a practice period to acclimatize to the content guide and to learn to associate it with areas that are particularly informative, while deemphasizing areas of the display that are not highlighted by the content guide. Future studies could use alternative methods of presenting the content guide, as the yellow ring was a simple application over the video that may not be the most optimal variant.

Half of the participants with hemianopia in a survey of video viewing habits expressed strong interest in assistive technology. One of the concerns with an intervention that modifies the displayed image is that it may be unacceptable to other viewers watching the same display. However, it seems that there would be plenty of opportunity to use such a guide, as watching television or video on a computer while alone was common, and, in a previous related study, the median number of TV sets per home was found to be two.

Though we found no difference between the participants with and without spatial neglect in this study, this does not mean that neglect may not affect the response to the content guide. All of the participants with neglect had mild neglect. So, it seems that people with mild neglect can benefit from the content guide. However, viewers with more severe neglect may have more difficulty with the IA task and may respond differently to the content guide.

In conclusion, we objectively demonstrated that participants with HH experienced difficulties acquiring information from video (reduced scores in our novel IA metric), and that the content guide provided a therapeutic benefit (increased IA scores), showing promise as a rehabilitation intervention for people with HH.

A Treatment for Spatial Neglect Using Guided Eye Movements

Spatial neglect (or unilateral neglect or visual neglect) is a debilitating cognitive impairment that frequently occurs as a result of stroke, traumatic brain injury and brain surgery. It is an inattention or failure to report or respond to stimuli on one side that cannot be attributed to sensory loss. Spatial neglect refers to a collection of related attention deficits that can occur with damage to any number of cortical or subcortical areas, usually in the right hemisphere.

People with spatial neglect have difficulties safely navigating through their environment. For example, they may bump into doorways and disregard potentially hazardous obstacles on the affected side (mobility deficits). People with spatial neglect may also fail to attend to one side of an object, even if a large part of the object is on their seeing side (e.g., eating food from only the right side of the plate) (visual search deficits). In addition to spatial deficits, neglect is frequently accompanied by a lack of awareness of one's deficits (anosognosia). This anosognosia and the lack of awareness of the affected side makes spatial neglect particularly difficult to treat using a patient-initiated approach, such as asking them to remember to look to the left every time they enter a new room, or scan to the left when they walk.

People with spatial neglect also present with non-spatial attention deficits in arousal and sustaining attention. The degree of non-spatial impairment correlates with spatial neglect severity across patients. Also, within an individual, moment-to-moment changes in non-spatial attentional resources can modulate spatial neglect symptoms. These findings have led to many approaches seeking to increase attention and arousal as a treatment for spatial neglect. Some seem to be effective in the short term, but these benefits have proven difficult to sustain over longer periods. A recent Cochrane Review concluded, "Several types of neglect specific approaches are now described but there is insufficient evidence to support or refute their effectiveness at reducing disability and improving independence" (Bowen A, et al (2013) *Cochrane Database Syst Rev.* 7: CD003586). Thus, there is a pressing need to assist people with spatial neglect.

Many treatments have been investigated for spatial neglect including occupational therapy, cognitive-based rehabilitation, mental practice, mirror therapy, voluntary trunk rotation, vestibular rehabilitation, electrical somatosensory stimulation, transcutaneous nerve stimulation, hemi-field eye-patching, prismatic glasses, peripheral prism glasses, visual target training, optokinetic stimulation, and visual scanning training (often, computer-based). One approach that has been widely adopted, despite little evidence of benefit, is visual scanning training. This training varies from simply providing instructions to the participant to scan to the neglected side, to the use of a visual-motor training device such as the Dynavision, a large wall-mounted board housing 64 small buttons that illuminate in random order. Training with the Dynavision or computer-based visual scanning. The Dynavision device is typically involves systematically directing the participant's gaze to targets across the entire visual field. However, evidence for the efficacy of such treatments is mixed, and seems to require many long training sessions (in one report, 40 sessions of 50 minutes each). Achieving compliance is a challenge, since the training is typically quite tedious. Visual training with computer-based methods has been shown to be effective over standard occupational therapy and visual (field) restoration (e.g. Modden C, et al. (2011) *Neurorehabil. Neural Repair.* 26(5): 463-9).

Another approach to treating spatial neglect involves having the participant watch a stimulus that drifts horizontally across the visual field. This can produce a series of involuntary eye movements characterized by a pursuit followed by saccade, followed by another pursuit and saccade, etc., or optokinetic nystagmus, which is an involuntary series of eye movements. In one example, a field of dots moves across a display placed in front of the participant. Typically, the drifting stimulus (e.g., dots) move from the attended side to the non-attended side, and the participant's task is to follow them (pursuit eye movement), and, when the end of the display is reached, to look back to the other side (saccade) and find a new dot or set of dots to follow. In a recently reported study, following 40 minute sessions of "smooth pursuit eye movement" training conducted over a one week period there were substantial improvements in various measures related to visual and auditory spatial neglect (Kerkhoff, G., et al. (2013) *Neurorehabil. Neural Repair.* 27: 789-798. Kerkhoff G, et al. (2014) *Neurorehabil. Neural Repair.* 28(6): 554-63 found that optokinetic training (that they call "smooth pursuit training") provided greater benefit than visual scanning training.

In an implementation, dynamic cueing can be used to treat spatial neglect. Dynamic cueing involves guiding eye movements with a localized stimulus that is continuously shifted in relation to the content of the presented scene. Typically, that stimulus can include the marker representing the region of interest or the important content. As an example, in a video of a person walking past a shop front, in which the person is of most interest, the stimulus would follow the person. Utilizing the content guide, the participant can be asked to direct their gaze to the stimulus. By having varied scenes in which the stimulus moved around much of the display over time, the participant would make many eye movements into the non-attended side. As with the smooth pursuit eye movement training described above, it is expected that making the eye movements into the non-attended side to follow the dynamic-cue stimulus will reduce symptoms of spatial neglect (Karnath H O. (1996) *J Neurol Neurosurg Psychiatry.* 60: 217-220).

Figure 5A:
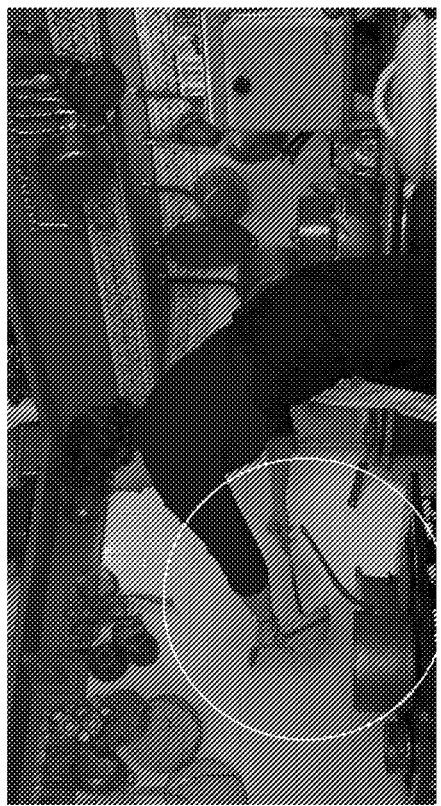
FIG. 5A illustrates a video frame with an overlaid ring as the content guide (stimulus for dynamic cueing).
Figure 5B:
FIG. 5B illustrates the video frame of FIG. 5A with a region of enhanced contrast as the content guide (dynamic cue stimulus). The location of the content guide (dynamic cue stimulus) in these video frames is the democratic region of interest.

For this approach, the scenes can be natural or constructed (e.g. computer generated). As an example, the scene could be a video of a busy street, or a cartoon. The content guide can be of any form that provided sufficient information to allow the participant to follow the content guide as a dynamic cue. For example, the content guide can be a ring (FIG. 5a) or a contrast enhanced region (FIG. 5b).

Example training-videos have been developed. These training videos include segments from commercially available media (e.g., Hollywood films) with the content guide (e.g., dynamic cue) superimposed. The location of the content guide in each frame is at the democratic center of interest. The democratic center of interest was derived from the eye movements of viewers with normal sight. Examples of video frames from these videos are shown in FIGS. 5A and 5B. The value of movies and other entertainment media (e.g. documentaries, television shows) includes that the material is engaging.

The eye movement patterns that occur with the content guide (e.g., dynamic cueing) includes smooth pursuits and fixations. As these are similar to those produced by smooth pursuit eye movement training (Kerkhoff G, et al. (2014) *Neurorehabil. Neural Repair.* 28(6): 554-63, and Kerkhoff, G., et al. (2013) *Neurorehabil. Neural Repair.* 27: 789-798), it is expected to be at least as effective as smooth pursuit eye movement training. Following the content guide (dynamic cue) stimulus while watching entertaining media should also be a more enjoyable task. Being more engaging, the dynamic cue treatment is expected to be engaging, thereby reducing the known problems with arousal or vigilance found among people with spatial neglect. Also, being a more enjoyable task than watching a display filled with drifting dots ("smooth pursuit training": Kerkhoff G, et al. (2014) *Neurorehabil. Neural Repair.* 28(6): 554-63, and Kerkhoff, G., et al. (2013) *Neurorehabil. Neural Repair.* 27: 789-798), the dynamic cue treatment is expected to provide better treatment compliance, which allows the possibility of treatments conducted outside the clinical setting, such as in-home treatment. Further, since the dynamic cue stimulus is at the democratic center of interest or similar location, it is related to the content of the scene and therefore is expected to provide greater benefit through the context. By being related to the contemporaneous context (i.e. the video content), the dynamic cue treatment is expected to make the association between the eye movements into the neglected side and the ongoing visual scene more obvious and relevant to real-world activities. Thus, the dynamic cue treatment may provide more benefit than smooth pursuit training. It is not known how optokinetic (smooth pursuit eye movement) training provides its benefit, though it has been speculated that the effect is related to shifts in attention and recalibration of egocentric orientation (Karnath H O. (1996) *J Neurol Neurosurg Psychiatry.* 60: 217-220). Consistent practice in following the cue to the neglected side is expected to improve neglect patients' habitual exploration patterns. Therefore, this approach is an improvement at least over the eye-movement stimulation therapies described above.

Example Treatment for Hemispatial Neglect Using Guided Eye Movements

Hemispatial neglect is a neuropsychological condition that often follows brain damage and results in patient failure to attend to the contralateral side of space. It has been shown that eye-movement training (specifically of smooth pursuit eye movements) can reduce neglect signs and improve the ability to perform daily activities. (Kerkhoff G, Reinhart S, Ziegler W, Artinger F, Marquardt C, Keller I. Smooth pursuit eye movement training promotes recovery from auditory and visual neglect: A randomized controlled study. Neurorehabil Neural Repair 2013; 27: 789-798.). Training has been shown to be effective. In the previous approach, training uses a field of dots that constantly drift towards the neglected size on a computer display. The participant's task is to look at a moving dot (which induces a pursuit eye movement) and when it disappears at the edge of the display, to look to the other side and find another dot to follow. This produces an optokinetic eye movement pattern (pursuit followed by a return saccade).

Some implementations of the dynamic cue highlights a segment of the display, for example with a circle or box, during a movie. In some implementations, the dynamic cue highlights the center of interest (COI), derived from the gaze data obtained from people normal vision (NV) as they watched the movie clip. As the movie progresses the dynamic cue moves around the display as the COI varies in location from frame to frame. This induces smooth pursuit eye movements that traverse into the neglected side. The dynamic cue reduces neglect signs and improves daily activities. Advantages of the dynamic cue include: (1) the task is more interesting and engaging for the participant so likely to be have better compliance; and (2) the induced eye movements are to locations that are meaningful, which will reinforce the value of eye movements into the neglected side. Thus, example implementations of the dynamic cue are improvements over existing treatment methods. In either the therapy scheme or the rehabilitation aide scheme, the systems lead to an improvement in daily activities, e.g., as reading and walking (safely).

An example treatment protocol is described. After five (about a week long) training sessions in which eye movements are guided into neglected and non-neglected visual regions, subjects may conclude that their hemispatial neglect has subsided or become less noticeable.

Participants complete seven sessions: #1 pre-test session; #2 to #6 training sessions; and #7 post-test session. Participants will have the option to do the first training session (session 2) on the same day as the pre-tests (session 1) and to do the post-tests (session 7) on the fifth day of training (session 6), or on different days.

Session 1 (pre-tests): clinical tests will be completed (e.g., visual acuity, contrast sensitivity, visual field), followed by neglect tests (e.g., KF-NAP, BITc, Open/Closed Loop Pointing) and the two daily-activity measures, paragraph reading (IReST Reading Test) and Information Acquisition (IA), which involves watching and describing twenty 30-second movie clips. Following session 1, the participant also will have the option to complete the first training (session 2) on the same day.

Sessions 2 to 6 (Training Sessions): Will each take about one hour. During each training session the participant will watch two 30-minute movie clips while following the dynamic guide with their eyes.

Session 7 (post-tests): The final visit will conclude with the same neglect tests that were done during the first visit (e.g., KF-NAP, BITc, Open/Closed Loop Pointing), and the same two daily-activity measures, paragraph reading (IReST Reading Test) and Information Acquisition (a different set of twenty 30-second movie clips). The participant has the option to do neglect and IA tests in conjunction with their final day of training (session 6), or at a separate visit.

Study Specific Procedures. Subjects will complete the Montreal Cognitive Assessment (MoVA) test. Nasreddine Z S, Phillips N A, Bedirian V, et al. The Montreal Cognitive Assessment, MoCA: A brief screening tool for mild cognitive impairment. J Am Geriatrics Soc. 2005; 53(4): 695-699. Neglect Tests will be administered before and after the five training sessions. These tests are the KF-NAP, BITc, and Open/Closed Loop Pointing.

1) The Kessler Foundation Neglect Assessment Process (KF-NAP™) test quantifies symptoms of spatial neglect by measuring functional difficulties. The test includes questions about daily life activities such as eating, shaving, and so forth. One of the authors of this measure is a potential future collaborator on this project: Dr. Anna Barrett, Kessler Foundation. The KF-NAP test is described in: Chen P, Hreha K, Fortis P, Goedert K M, Barrett A M. Functional Assessment of Spatial Neglect: A Review of the Catherine Bergego Scale and an Introduction of the Kessler Foundation Neglect Assessment Process. Topics in stroke rehabilitation. 2012; 19(5): 423-435. doi:10.1310/tsr1905-423.

2) The Behavioural Inattention Test Concentional subtest (BITc) is a test for behavioral inattention. The test asks participants to draw shapes, cut lines in half with a pencil, and circle stars. The test assesses unilateral visual neglect and visual inattention. Wilson B A, Cockburn J, Halligan P W. Behavioural inattention test: A new approach to the testing of UVN. Thames Valley Test Company, Fareham, Hants, 1987.

3) Open and Closed Loop Pointing is an important neglect measure because it includes visuomotor functionality, unlike some of the other neglect tests. It is possible to have hemispatial neglect and have relatively normal visuomotor function. In other words, some people with hemispatial neglect will be able to point to the middle of a target as instructed while others will not. Therefore, this test helps describe the full picture of a patient's hemispatial neglect in terms of spatial parameter, visual function, and motor ability. Harvey, M. Muir, K. Reeves, I. Duncan, G. Livingstone, K. Jackson, H. Castle, P. Rossit, S. Pointing and bisection in open and closed loop reaching in patients with hemispatial neglect. Journal of Vision, 2008; 8(6):305, 305a Two measures of daily-living activities will be completed before and after the five training sessions:

4) iReST Reading Test (International Reading Speed Texts) will be simulated on a computer display (the IReST test is usually administered on printed pages). The task is reading short paragraphs (154 words on average). Gaze will be monitored as the participant reads out loud. Participants will be tracked for accuracy (word errors), speed, and the number of "backtracking" events. Their reading will be recorded (audio file) for post-hoc scoring of accuracy and errors. Trauzettel-Klosinski Dietz K, IReST Group. Standardized assessment of reading performance: The new international reading speed texts IReST. Investigative Ophthalmology & Visual Science, 2012; 53 (9): 5452-5461

5) Information Acquisition (IA) procedures. In order to complete IA, subjects will watch twenty 30-second Hollywood movie clips and will provide an oral description of each clips on its completion. The responses will be recorded (audio file). These descriptions of the clips will be transcribed and then compared to our database of natural-language responses from a large control group (people with normal vision). IA scores are an objective measure found using custom-software that uses natural-language processing. It is an approved procedure in IRB protocol 12-121H "Watching Television and Movies with Low Vision".

In some implementations, the treatment can be conducted by the patient with the assistance of a care giver in the home. For that, a tablet (e.g. iPad) can be provided that can present the treatment, track when the sessions were conducted and can use facial recognition to confirm that the patient actually was watching the clip (treatment). The built-in tracking and facial recognition are features that measure compliance with the treatment regimen.

A reading test and the information acquisition (IA) test can be used to measure the effects of the treatment on daily-living activities. Reading is difficult for people with neglect, as they do no pay attention or have reduced attention to things on the neglect side (most commonly on the left from a right-side brain injury), and thus they may not see all of a word (e.g. not see a letter or two on the left) and may have page navigation problems (e.g. do not get to the start of the next line, and instead start reading part of the way through the line of text). The IA test here is not so much about watching video, but instead it is a surrogate for the ability to comprehend the visual scene (i.e. if you cannot figure out what is happening, it is difficult to have normal interactions). Additional tests can include a measure of (pedestrian) mobility. People with neglect often have collisions with objects that they do not notice such as furniture and door frames. Such a test can have the patient walk a known course and their progress be measured in terms of time and "events" (e.g. collisions, hesitations).

Additional Variations

Although a few variations have been described in detail above, other modifications or additions are possible. For example, the region of interest may be marked or identified by any method that alerts the viewer to its presence. For the above study, a circle was employed. Alternative methods can include a rectangle or other regular polygon, illusory figures such as the Kaniza configuration, irregular polygons, highlighting through manipulations of contrast or color, or enhancement of the region of interest such as the addition of edge enhancement. Also, the region of interest can be an irregular shape and can vary in size and shape from video frame to frame, as illustrated in FIG. 2A, and the content guide might vary in its shape and size accordingly.

Figure 10:
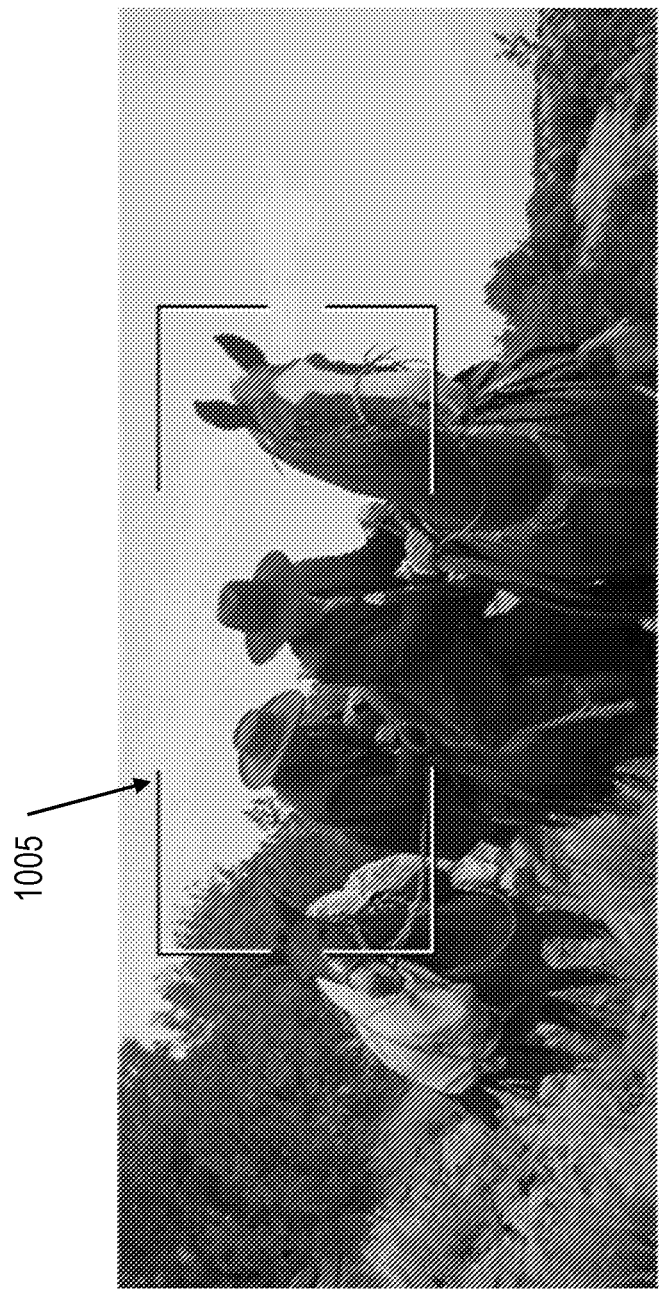
FIG. 10 illustrates a video frame with an example content guide taking the form of a Kaniza configuration.
Figure 11:
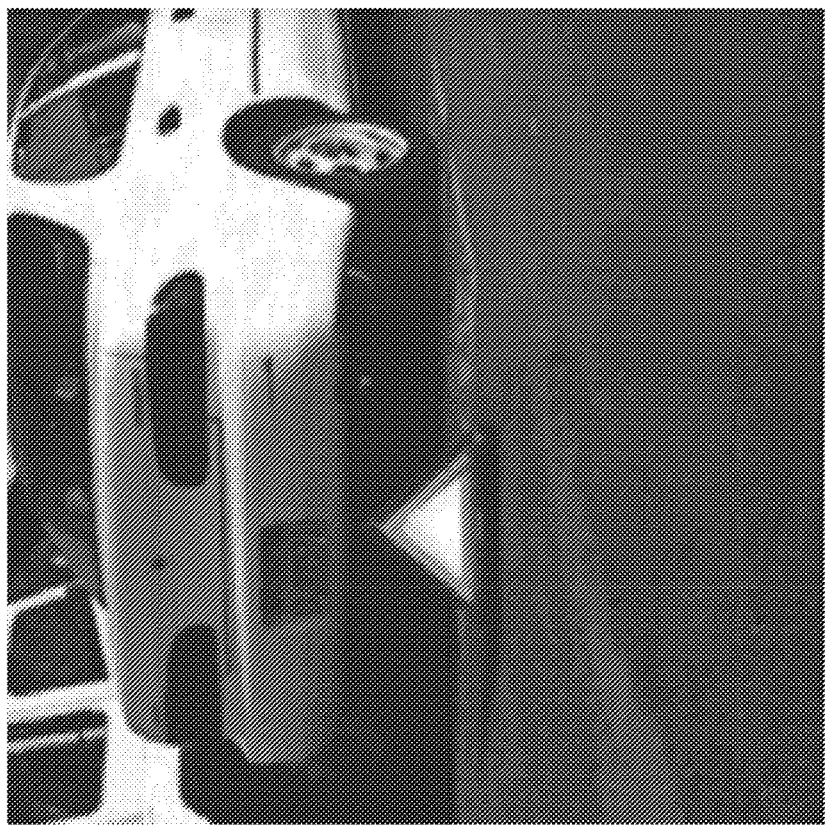
FIG. 11 is an image illustrating visual "pop-out" in which a unique visual target (e.g. a red dot) can be rapidly detected among a set of "homogeneous distractors" (e.g. many blue dots).

FIG. 10 illustrates a video frame with an example content guide 1005 taking the form of a Kaniza configuration. This approach can provide a benefit in that over some parts (e.g. sky) the black line is most visible, while over other parts of the scene (e.g. horse) the white line is most visible. Despite the swapping from segments that are "white" to segments that are "black", a continuous contour that forms a rectangle is seen. And, it has high visual salience in that is seen very quickly without any conscious attention or visual search (e.g., it pops out). FIG. 10 is photograph showing an example of an image containing a content guide or dynamic cue with high visual salience. For example, the color and contrast differs measurably from the color and contrast compared to the areas of the image surrounding the triangle (exemplary region with high visual salience). FIG. 11 is a photograph showing an example of an image containing a content guide or dynamic cue with high visual salience. The image contains bipolar lines (black outside white). The benefit is that over some parts (e.g. sky) the black line is most visible, while over other parts of the scene (e.g. horse) the white line is most visible. Despite the swapping from segments that are "white" to segments that are "black", a continuous contour that forms a rectangle is visually perceived. The exemplary image has high visual salience in that one sees the bracketed region very quickly without any conscious attention or visual search (i.e., it pops out).

Visual salience involves the detection of locations whose local visual attributes significantly differ from the surrounding image attributes, along some dimension or combination of dimensions. This significant difference could be in a number of simple visual feature dimensions which are believed to be represented in the early stages of cortical visual processing: color, edge orientation, luminance, contrast, or motion direction. A high level of difference of these parameters is referred to as high visual salience and leads to a perception of "pop-out" of the region of the reference image.

In vision research, visual "pop-out" is well known in the art. The term refers to the phenomenon in which a unique visual target (e.g. a red dot) is rapidly detected among a set of "homogeneous distractors" (e.g. many blue dots) (Treisman A M. Preattentive processing in vision. Comput Vis Graph Image Proc. 1985; 31:156-177; Wolfe J M. Guided search 2.0: A revised model of visual search. Psychonomic Bulletin and Review. 1994; 1:202-238). It can refer to a feature with very high visual salience within a scene (Treisman A. & Gelade G. (1980). A feature integration theory of attention. Cognitive Psychology 12:97-136; Itti L & Koch C (2001). Computational Modeling of Visual Attention. Nature Reviews Neuroscience 2(3):194-203) Visual salience is the distinct subjective perceptual quality that makes some items in a scene stand out from their neighbors and immediately grab attention. The principle behind computing salience is the detection of locations whose local visual attributes significantly differ from the surrounding image attributes, along some dimension or combination of dimensions. This significant difference could be in a number of simple visual feature dimensions which are believed to be represented in the early stages of cortical visual processing: color, edge orientation, luminance, or motion direction. Visual salience can be measured computationally (image processing) or by using visual psychophysical means. The methods and systems described herein include a defining feature of an appropriate stimulus for the content guide or dynamic cue is that it has high visual salience across the scenes within the video of interest, such the content guide or dynamic cue pops out in almost all frames of the video.

For the above described study, the region of interest was identified using the gaze patterns of a control group consisting of people with normal vision who watched each video clip. Other methods could be employed to identify the region of interest. For example, an image processing method. Such methods are becoming much better at identifying the regions of interest (e.g. Bylinskii Z, et al. (2017) MIT Saliency Benchmark, accessed Jan. 6, 2017; using the term "salience" and "saliency models"). Using such a method is an alternative that allows identification of the region of interest from the video content alone, using computer algorithms. A hybrid method can be employed that combines computer algorithms with human gaze data.

If human gaze locations are to be used to determine the region of interest, the approach to determining the region of interest and marker can vary based on whether the video is pre-recorded material (e.g., most TV shows) and live broadcast. For movies and similar pre-recorded material, there can be little additional cost (relative to total cost) for the region of interest to be determined and provided along with the audio track. Like the Descriptive Video Service that provides auditory descriptions of some programs, the region of interest can be determined for some, but not all, programs at a moderate cost that is comparable to the Descriptive Video Service. In addition, there is the possibility of viewers paying a modest subscription fee for the region of interest information. Region of interest data could be obtained using a distributed service such as Amazon Mechanical Turk under which workers are paid to perform tasks, which in this case would be to watch video content. Many current computers contain a camera that views the user (e.g., "webcam"). Software that allows a user to control the mouse cursor with head movements and numerous webcam-based eye-tracking systems are available. Internet users watching video content can provide gaze data to a central repository, similar to distributed computing projects.

Providing region of interest information using human gaze data for live broadcast can require infrastructure and introduce a delay. One approach can be to have a small (e.g. ten or twelve) group of viewers watching the live video feed while their gaze was tracked. The gaze data can be processed quickly, currently in a few seconds, after which, the material can be broadcast. Such a delay can be similar to the delay used in many live radio broadcasts, in which the delay is used to allow deletion of inappropriate content such as swear words by an engineer or producer.

The content guide serves to manipulate the gaze pattern of a viewer away from where the viewer might otherwise, without the content guide, look at any moment while viewing the video. In some implementations, the content guide can be used to manipulate the gaze pattern of a viewer with normal vision. This can be performed in situations in which there is some benefit or purpose to an alteration away from the natural gaze pattern. Thus, the content guide can be used to alter the viewer to material or objects in the video that might otherwise not be fixated (placed at the gaze center, and thus explicitly viewed). Salient objects can be neglected when viewing video by people with normal vision (inattentional blindness: Neisser, U. & Becklen, R. (1975). *Cognitive Psychology,* 7(4), 480-494; Simons, D. J. & Chabris, C. F. (1999). *Perception,* 28(9), 1059-1074). The content guide can be used to alert the viewer to such salient or important content.

The subject matter described herein provides many technical advantages. For example, some hemianopic patients and other with central vision loss are housebound, especially elderly patients. When used for rehabilitation, the current subject matter can be implemented for housebound patients. This avoids the difficulty of bringing patients into clinics for treatment (or bringing equipment and personnel to patients' homes).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for reducing or treating one or more symptoms of hemianopia or spatial neglect in a patient in need thereof, the hemianopia or the spatial neglect being a result of a brain injury to the patient, the method comprising:
   positioning the patient in front of a display,
   providing a video clip or an image on the display,
   marking a region of interest on the video clip or image with a dynamic cue or content guide, wherein the region of interest on the video clip is determined by at least tracking gaze patterns of a plurality of healthy patients, wherein the region of interest is determined using a measure of a central tendency of a two-dimensional distribution of gaze points of a majority of the plurality of healthy patients viewing the video clip or image, and
   thereby reducing or treating one or more symptoms of hemianopia or spatial neglect in the patient.

2. The method of claim 1, wherein the patient is positioned in front of the display at a distance of 10 cm, 20 cm, 30 cm, 40 cm, 50 cm, 60 cm, 70 cm, 80 cm, 90 cm, 100 cm, 200 cm, 300 cm, 400 cm, 500 cm, 600 cm, 700 cm, 800 cm, 900 cm, 1000 cm, 2000 cm, 3000 cm, 4000 cm, or 5000 cm.

3. The method of claim 1, further comprising, calculating the Information Acquisition (IA) score of the patient comprising a hemianopia.

4. The method of claim 3, further comprising comparing the IA score of the patient comprising a hemianopia to control IA score or IA score of a healthy patient.

5. The method of claim 1, wherein the video clip is from 5 seconds to 3 hours.

6. The method of claim 1, wherein the content guide comprises a color and a shape.

7. The method of claim 6, wherein the color comprises yellow, red, black, white, cyan, or blue; and wherein the shape comprises a circle, rectangle, outline, polygon, or two hemi-circles.

8. The method of claim 1, wherein the region of interest is updated every 0.017, 0.033, 0.066, 0.0099, 0.0132, 0.0165, 0.0198, 0.0231, 0.0264, 0.0297, 0.033, 0.0363, 0.0396, 0.0429, 0.0462, 0.0495, 0.0528, 0.0561, 0.0594, 0.0627, 0.066, 0.0693, 0.0726, 0.0759, 0.0792, 0.0825, 0.0858, 0.0891, 1, 2, 3, 4, 5, 6, 8, 10 seconds, every 20 seconds, every 30 seconds, every 60 seconds, every 90 seconds, or every 120 seconds.

9. The method of claim 1, wherein the display comprises a portable device, a computer, a cinema screen, a photograph, or a television.

10. The method of claim 1, wherein the hemianopia is the result of a traumatic brain injury (TBI), a stroke, a stroke during surgery, congenital and intentional consequence of surgery, or a brain tumor.

11. The method of claim 10, wherein the stroke comprises ischemic stroke or hemorrhagic stroke.

12. The method of claim 1, wherein the method is continued every 24 hours, every 48 hours, or every 96 hours.

13. The method of claim 1, wherein the method is continued on a regime of every four days, every week, every 10 days, every 14 days, every month, every 2 months, every 3 months, or every 4 months.

14. The method of claim 1, wherein the region of interest is determined using a kernel density estimate of gaze points of a majority of the plurality of healthy patients viewing the video clip or image.

15. A method for reducing or treating one or more symptoms of a cognitive disorder in a patient in need thereof, the cognitive disorder being a result of a brain injury to the patient, the method comprising:
   positioning the patient in front of a display,
   providing a video clip or an image on the display,
   marking a region of interest on the video clip or image with a content guide, wherein the region of interest on the video clip is determined by at least tracking gaze patterns of a plurality of healthy patients, wherein the region of interest is determined using a measure of a central tendency of a two-dimensional distribution of gaze points of a majority of the plurality of healthy patients viewing the video clip or image, and
   thereby reducing or treating one or more symptoms of the cognitive disorder in the patient.

16. The method of claim 15, wherein the patient is positioned in front of the display at a distance of 10 cm, 20 cm, 30 cm, 40 cm, 50 cm, 60 cm, 70 cm, 80 cm, 90 cm, 100 cm, 200 cm, 300 cm, 400 cm, 500 cm, 600 cm, 700 cm, 800 cm, 900 cm, 1000 cm, 2000 cm, 3000 cm, 4000 cm, or 5000 cm.

17. The method of claim 15, wherein the cognitive disorder comprises Attention Deficit Hyperactivity Disorder (ADHD), Attention Deficit Disorder (ADD), Alzheimer's disease, or dementia.

18. A system for reducing or treating one or more symptoms of hemianopia or spatial neglect in a patient in need thereof, the hemianopia or the spatial neglect being a result of a brain injury to the patient, the system comprising:
a display configured to provide a video clip or an image and to mark a region of interest on the video clip or image with a dynamic cue or content guide thereby reducing or treating one or more symptoms of hemianopia or spatial neglect in the patient, wherein the region of interest on the video clip is determined by at least tracking gaze patterns of a plurality of healthy patients, wherein the region of interest is determined using a measure of central tendency of a two-dimensional distribution of gaze points of a majority of the plurality of healthy patients viewing the video clip or image.

19. The system of claim 18, they system further comprising:
a camera configured to acquire an image of the patient when the patient is positioned in front of the display; and
facial recognition circuitry configured to identify, using the acquired image, an identity of the patient to assess compliance with a spatial neglect or hemianopia treatment protocol.

20. The system of claim 18, wherein the content guide comprises a color and a shape.

21. The system of claim 20, wherein the color comprises yellow, red, black, white, cyan, or blue; and wherein the shape comprises a circle, rectangle, outline, polygon, or two hemi-circles.

22. The system of claim 18, wherein the region of interest is updated every 0.017, 0.033, 0.066, 0.0099, 0.0132, 0.0165, 0.0198, 0.0231, 0.0264, 0.0297, 0.033, 0.0363, 0.0396, 0.0429, 0.0462, 0.0495, 0.0528, 0.0561, 0.0594, 0.0627, 0.066, 0.0693, 0.0726, 0.0759, 0.0792, 0.0825, 0.0858, 0.0891, 1, 2, 3, 4, 5, 6, 8, 10 seconds, every 20 seconds, every 30 seconds, every 60 seconds, every 90 seconds, or every 120 seconds.

23. The system of claim 18, wherein the display comprises a portable device, a computer, a cinema screen, a photograph, or a television.

* * * * *